US012672986B2

(12) United States Patent
Dalal et al.

(10) Patent No.: US 12,672,986 B2
(45) Date of Patent: Jul. 7, 2026

(54) ABSORBENT ARTICLE WITH LAMINATE BOND PATTERN

(71) Applicant: The Procter & Gamble Company, Cincinnati, OH (US)

(72) Inventors: Urmish Popatlal Dalal, Milford, OH (US); Astrid Annette Sheehan, Symmes Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 435 days.

(21) Appl. No.: 18/320,293

(22) Filed: May 19, 2023

(65) Prior Publication Data

US 2023/0372164 A1　Nov. 23, 2023

Related U.S. Application Data

(60) Provisional application No. 63/426,429, filed on Nov. 18, 2022, provisional application No. 63/344,277, filed on May 20, 2022.

(51) Int. Cl.
　A61F 13/15　　　(2006.01)
　A61F 13/49　　　(2006.01)
　A61F 13/51　　　(2006.01)

(52) U.S. Cl.
　CPC .............................. A61F 13/4902 (2013.01); *A61F 2013/49022* (2013.01); *A61F 2013/49023* (2013.01);
(Continued)

(58) Field of Classification Search
　CPC .............. A61F 13/4902; A61F 13/5633; A61F 2013/49023; A61F 2013/49022;
(Continued)

(56) References Cited

U.S. PATENT DOCUMENTS 5,224,405 A * 7/1993 Pohjola .................. B65H 29/24
　　　　　　　　　　　　　　　　　　　156/519
6,677,258 B2 * 1/2004 Carroll ................. D04H 1/4291
　　　　　　　　　　　　　　　　　　　442/394

(Continued)

FOREIGN PATENT DOCUMENTS

WO　　　2012036599 A1　　3/2012
WO　　　2021252442 A1　　12/2021

OTHER PUBLICATIONS

16262M PCT Search Report and Written Opinion for PCT/US2023/022803 dated Sep. 12, 2023, 12 pages.

*Primary Examiner* — Jacqueline F Stephens
(74) *Attorney, Agent, or Firm* — Daniel S. Albrecht

(57)　　　　　　ABSTRACT

An absorbent article includes a first and second waist region and a crotch region disposed between the first and second waist regions. The absorbent article includes a chassis having a topsheet, backsheet, and an absorbent core disposed between the topsheet and the backsheet. A laminate may be joined to the chassis. The laminate is an ultrasonically bonded laminate having a bond pattern. The bond pattern includes a plurality of discrete, primary ultrasonic bonds and a plurality of secondary ultrasonic bonds. The primary bonds may permanently attach the one or more layers of the laminate and the secondary bonds may releasably attach the one or more layers of the laminate. The releasable bond may release one or more layers of the laminate when the laminate is extended in the stretch direction.

20 Claims, 14 Drawing Sheets

(52) U.S. Cl.
CPC ............... *A61F 2013/49031* (2013.01); *A61F*
*2013/49033* (2013.01); *A61F 2013/49034*
(2013.01); *A61F 2013/49047* (2013.01); *A61F*
*2013/51083* (2013.01)

(58) Field of Classification Search
CPC .. A61F 2013/49031; A61F 2013/49034; A61F
2013/49033; A61F 2013/49047; A61F
2013/51083
See application file for complete search history.

(56) References Cited

U.S. PATENT DOCUMENTS

| | | | |
|---|---|---|---|
| 7,156,833 B2 * | 1/2007 | Couture-Dorschner ..................... A61F 13/49001 604/385.03 | |
| 8,353,889 B2 * | 1/2013 | Back ..................... A61F 13/565 604/394 | |
| 9,533,067 B2 * | 1/2017 | Schonbeck ....... A61F 13/49019 | |
| 10,894,386 B2 | 1/2021 | D'aponte et al. | |
| 11,642,248 B2 | 5/2023 | Dalal | |
| 12,303,366 B2 | 5/2025 | Ashraf et al. | |
| 2017/0348158 A1 * | 12/2017 | You ................... A61F 13/15804 | |
| 2018/0042785 A1 * | 2/2018 | Dalal ...................... A61F 13/84 | |
| 2022/0387232 A1 | 12/2022 | Raycheck et al. | |
| 2023/0107550 A1 | 4/2023 | Ferguson et al. | |

* cited by examiner

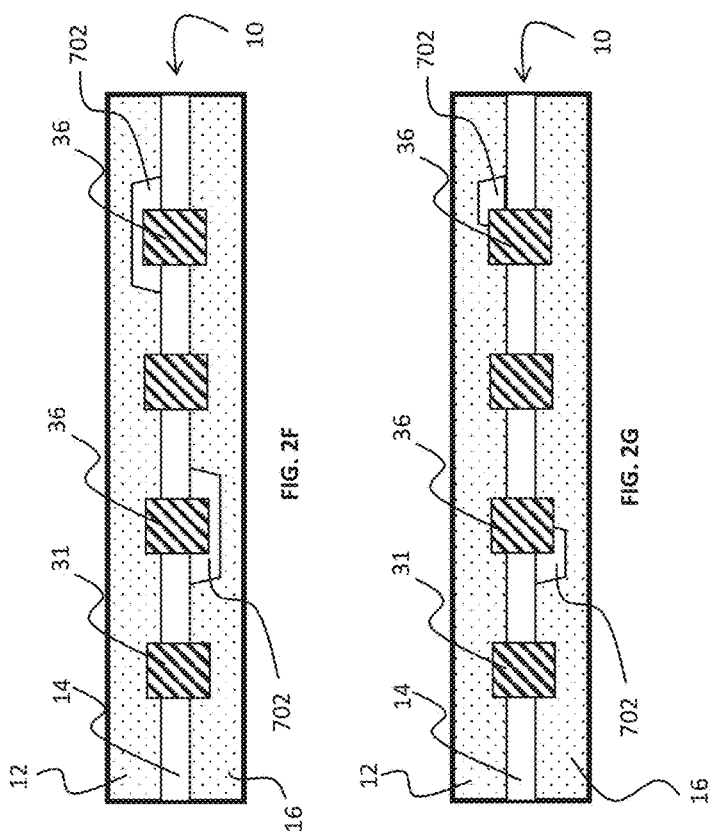
FIG. 2F
FIG. 2G
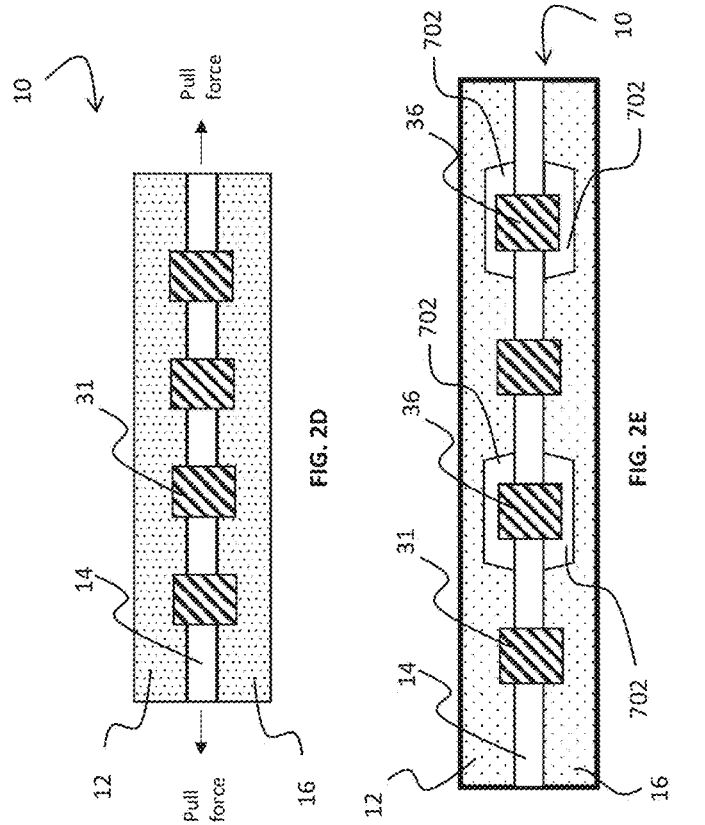
FIG. 2D
FIG. 2E

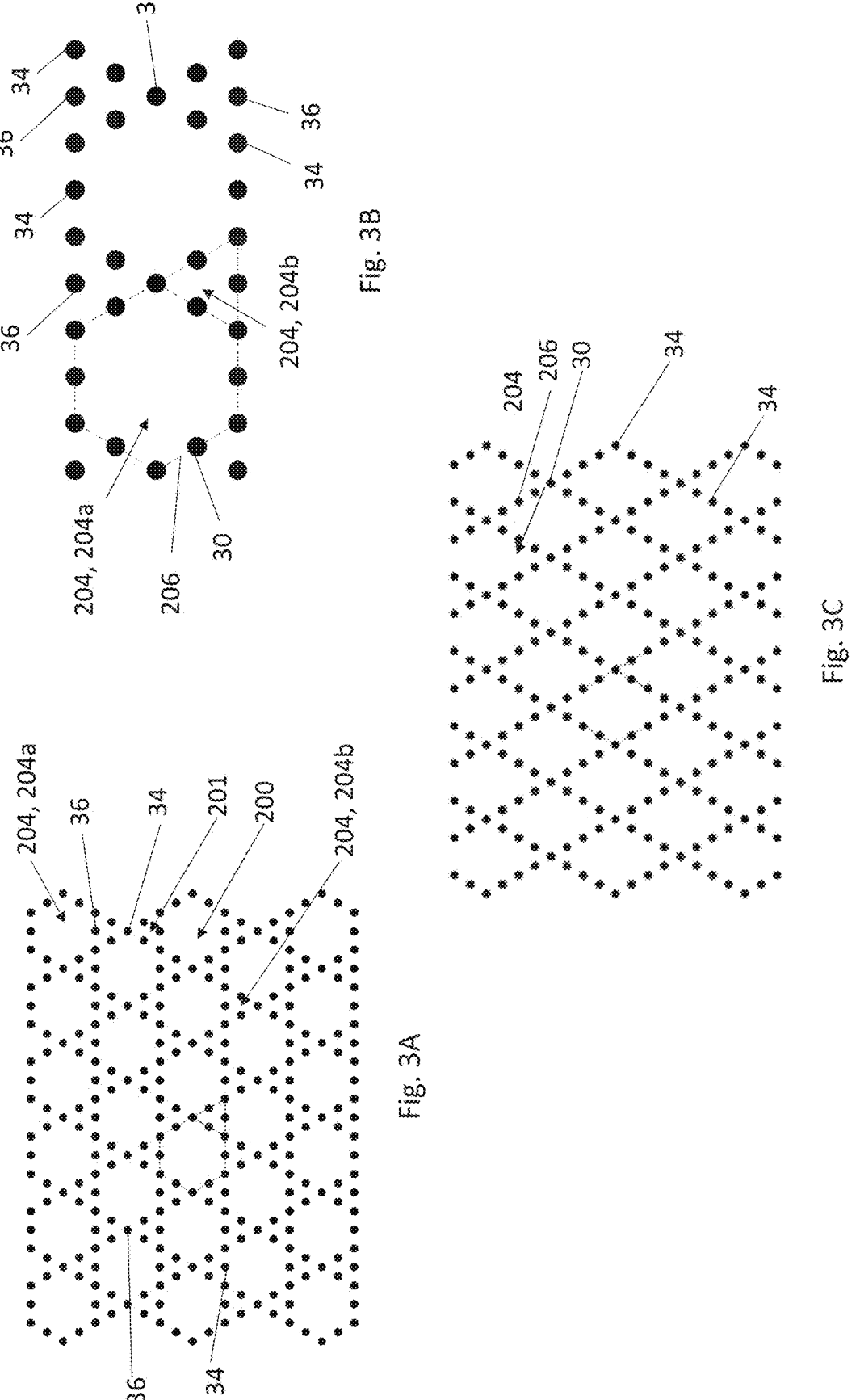

ABSORBENT ARTICLE WITH LAMINATE BOND PATTERN

FIELD

The present disclosure relates to absorbent articles having stretch laminates with bond patterns. More specifically. the present disclosure related to stretch laminates including one or more permanent bonds and one or more releasable bonds.

BACKGROUND

Elastomeric laminates are used in various products including absorbent articles (e.g., diapers, incontinence articles, feminine hygiene pads). Such laminates typically include an elastomeric layer that provides extensibility to the laminate and an outer layer that is less stretchable but suitable for providing durability and desirable tactile properties. In this way, the laminate permits a component of an article to closely and comfortably contact the wearer while providing desirable exterior qualities.

Layers of the elastomeric laminate may be combined by various means, including for example thermal bonds in a gathered laminate configuration where corrugations are present in one or more layers. In bonding the layers, manufacturers must balance strength, extensibility, and comfort considerations. These considerations, however, often counteract one another. For example, while more bonds may provide greater lamination strength, it may undermine extensibility. Likewise, more resilient materials may provide greater tear resistance but less softness or breathability.

Therefore, there is a continued need to balance strength, comfort, and extensibility for stretch laminates. There is also a need to provide bond patterns that maximize desired laminate properties while minimizing undesirable traits. Further, there is a need to convey laminate properties through bond patterns.

SUMMARY

An absorbent article including a topsheet, a backsheet, and an absorbent core disposed between the topsheet and the backsheet. The absorbent core includes at least one elastic ear having a laminate. The laminate includes an elastomeric layer and a nonwoven layer. The laminate may include a plurality of discrete primary ultrasonic bonds and a plurality of secondary ultrasonic bonds. The elastomeric layer and the nonwoven layer remain permanently attached by the primary ultrasonic bonds and releasably attached by the secondary ultrasonic bonds. The secondary ultrasonic bonds release when the laminate is extended greater than about 5 mm in a stretch direction.

An absorbent article including a topsheet, a backsheet, and an absorbent core disposed between the topsheet and the backsheet. The absorbent core includes at least one elastic ear having a laminate. The laminate includes an elastomeric layer and a nonwoven layer. The laminate may include a plurality of discrete primary ultrasonic bonds and a plurality of secondary ultrasonic bonds. The elastomeric layer and the nonwoven layer remain permanently attached by the primary ultrasonic bonds and releasably attached by the secondary ultrasonic bonds. The secondary ultrasonic bonds release when the laminate is extended by at least 0.5 N/in force in a stretch direction.

An absorbent article including a topsheet, a backsheet, and an absorbent core disposed between the topsheet and the backsheet. The absorbent core includes at least one component having a laminate. The laminate includes an elastomeric layer and a nonwoven layer. The laminate may include a plurality of discrete primary ultrasonic bonds and a plurality of secondary ultrasonic bonds. The elastomeric layer and the nonwoven layer remain permanently attached by the primary ultrasonic bonds and releasably attached by the secondary ultrasonic bonds. The secondary ultrasonic bonds release when the laminate is extended greater than about 5 mm in a stretch direction.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawing.

FIG. 2D is a schematic illustration of a stretch laminate being subjected to a lateral pull force.

FIGS. 2E-2G is a schematic illustration of a stretch laminate with various types of releasable bond sites after being subjected to a lateral pull force.

FIGS. 3A-3C are schematic representations of exemplary patterns for a laminate according to nonlimiting embodiments of the present disclosure.

DETAILED DESCRIPTION

Definitions

Figure 2A:
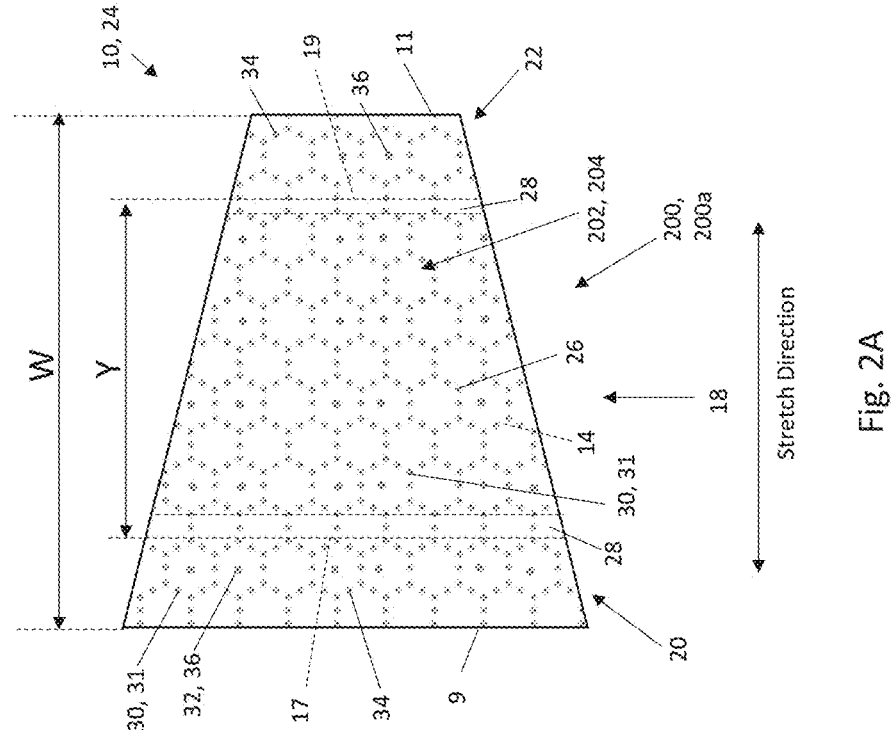
FIG. 2A is a plan view of an exemplary laminate according to a nonlimiting embodiment of the present disclosure.

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Elastic," "elastomeric," and "elastically extensible" mean the ability of material, or portion of the material, to stretch by at least 50% without rupture or breakage at a given load, and upon release of the load the elastic material or component exhibits at least 70% recovery (i.e., has less than 30% set) in one of the directions as per the Hysteresis Test described herein. Stretch, sometimes referred to as strain, percent strain, engineering strain, draw ratio, or elongation, along with recovery and set may each be determined according to the Hysteresis Test described in more detail below. Materials that are not elastic are referred as inelastic. As used herein, a laminate is elastic if at least 20% of the area of the laminate meets the elastic definition herein. In this situation, the percent of area of the laminate is determined when the laminate is in a fully stretched state.

"Extensible" means the ability to stretch or elongate, without rupture or breakage, by at least 50% as per step 5(a) in the Hysteresis Test herein. As used herein, a laminate is extensible if at least 20% of the area of the laminate meets the extensible definition herein. In this situation, the percent of area of the laminate is determined when the laminate is in a fully stretched state. If a laminate does not meet the definition of elastic above, but does meet the definition of extensible provided in this paragraph, the laminate is an extensible laminate.

"Fully stretched" in reference to a laminate means (1) for corrugated laminates, the laminate is fully stretched when corrugations are substantially flattened by extending the laminate while making sure that the inelastic substrates of the laminate are not plastically deformed, and (2) for laminates without corrugations, the laminate is considered fully stretched without any such extension (i.e., noncorrugated laminates are fully stretched in their relaxed state). "Relaxed" in reference to a laminate means at rest with substantially no external force acting on the laminate, other than gravity.

"Unit" is the smallest building block of a pattern, whose geometric arrangement defines pattern's characteristic imagery and whose repetition in space is necessary to re-construct the pattern. A pattern may be formed from one or more units. A "repeating unit" is a unit that is present multiple times within a pattern; said unit may be rotated, mirrored, or otherwise reoriented.

"Closed cell unit" means a unit that is identifiable a shape having a perimeter, the perimeter being formed by at least 5 bonds substantially surrounding an area free of permanent bonds. The perimeter may be formed by discontinuous bonding. For example, discrete bonds that are sufficiently small and/or close together that the viewer sees a shape substantially surrounded by a perimeter. Closed cell units may share bond sites with each other to form closed cell.

"Releasable bond" in relation to a laminate means the bond will release upon stretching the laminate in the in-use stretch direction from the relaxed state of the laminate. Release includes at least partial separation of the bond. For example, one or more fibers of the nonwoven portion of the laminate may remain bonded at the bond site upon extension of the laminate. However, despite these one or more fibers remaining bonded, the bond site will be considered released.

"Permanent bond" in relation to a laminate means the bond will remain intact upon stretching the laminate by at least 15 mm in the transverse direction from the relaxed state of the laminate, according to the Laminate Extension Test Method.

"Joined" refers to configurations whereby an element is directly secured to another element by affixing the element directly to the other element and to configurations whereby an element is indirectly secured to another element by affixing the element to intermediate member(s) which in turn are affixed to the other element.

Overview

Figure 1:
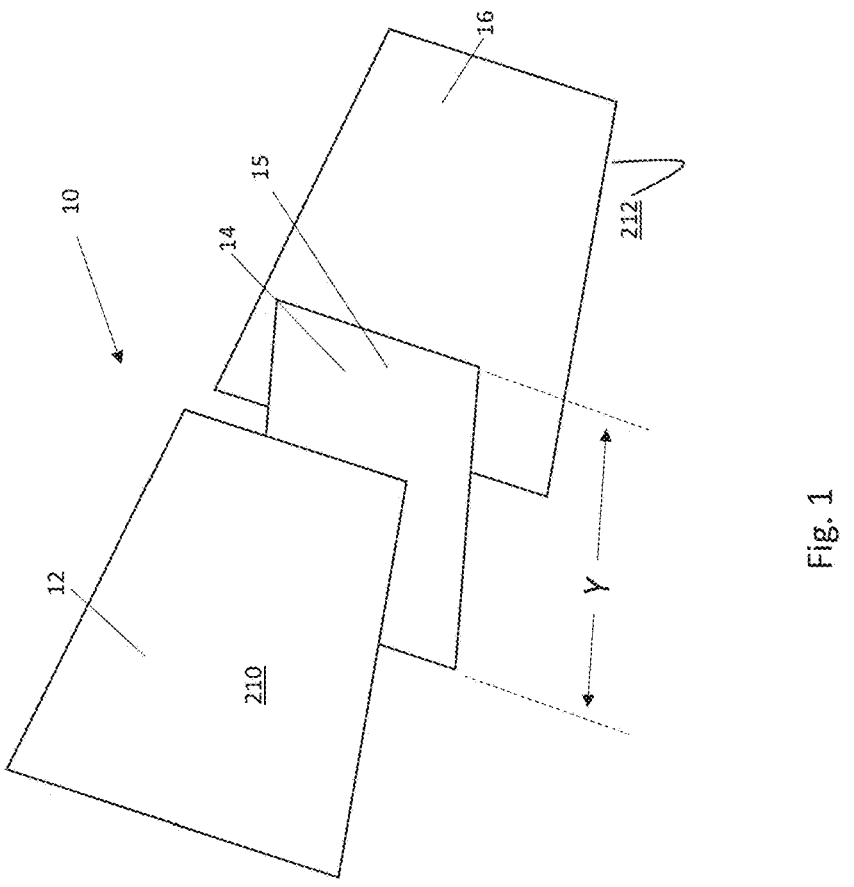
FIG. 1 is an exploded perspective view of an exemplary laminate according to a nonlimiting embodiment of the present disclosure.

As shown in FIG. 1, a laminate 10 includes a first coverstock layer 12 and an elastomeric layer 14. The laminate may include a second coverstock layer 16, and the elastomeric layer 14 may be sandwiched between the first and second coverstock layers. Coverstock layer materials may be non-elastic. Additional layers may be included. Layers may be nonwovens, inelastic materials, elastic, or extensible materials. The laminate may be extensible. In certain embodiments, the laminate is elastomeric. Two or more laminate layers may be joined by a plurality of bonds 30 as shown in FIG. 2A. The bonds may be ultrasonic bonds 31, which may join nonwoven layers through the elastomeric layer. An ultrasonically bonded laminate may be formed by any suitable processes, including but not limited to those described in commonly assigned U.S. Pat. Nos. 10,568,775; 10,568,776; and 10,575,993. The bonds may be any suitable shape or size such that two or more laminate layers are joined.

Figure 2C:
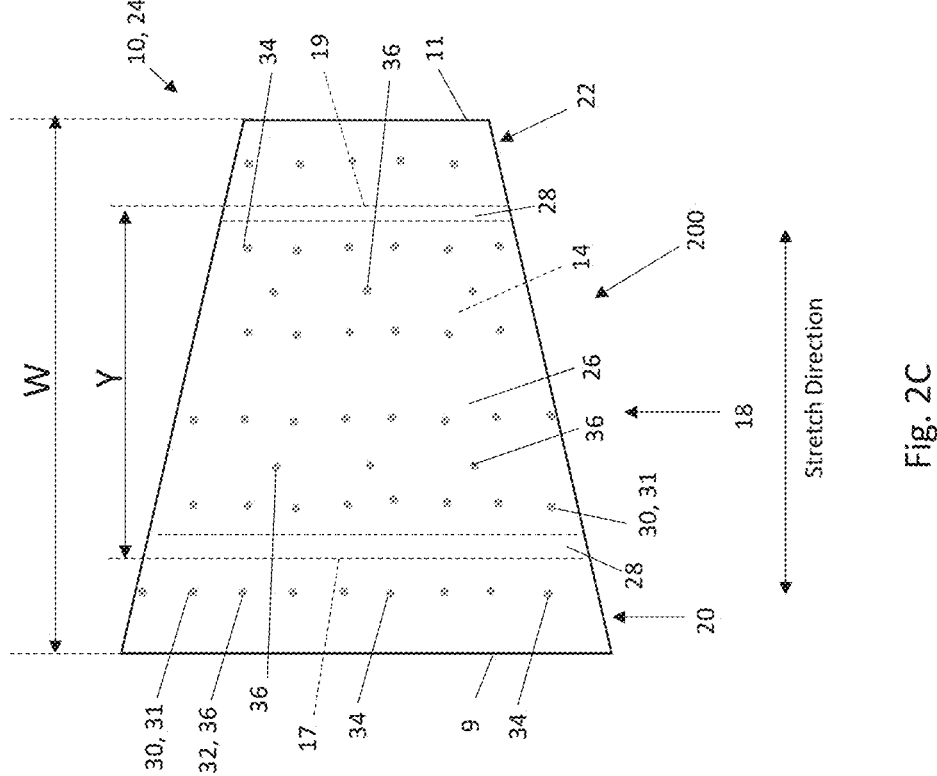
FIG. 2C is a plan view of an exemplary laminate according to a nonlimiting embodiment of the present disclosure.
Figure 2B:
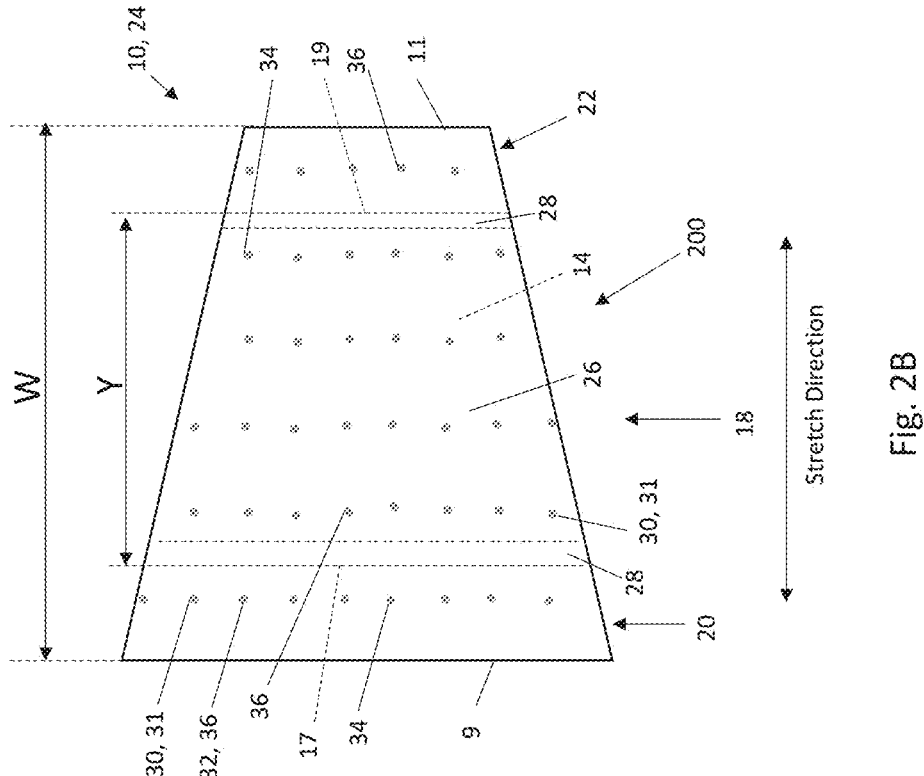
FIG. 2B is a plan view of an exemplary laminate according to a nonlimiting embodiment of the present disclosure.

As illustrated in FIGS. 2A-2C, the laminate may include a plurality of bonds 30, which may be ultrasonic bonds 31. The plurality of bonds may be arranged in a bond pattern. The bond pattern may include a plurality of bonds arranged in a grid configuration or a shaped configuration, such that a groups of bonds form one or more shapes. For example, as illustrated in FIG. 2A, the laminate includes a first bond pattern 200. The first bond pattern 200 includes closed cell units 204. The laminate may include one or more bond patterns and these bond patterns may be different.

The bonds of a bond pattern may include a Bond Separation Distance of from about 0.1 mm to about 15 mm or from about 1.2 mm to about 10 mm or from about 1.5 mm to about 5 mm or less than about 5 mm, according to the Bond Dimension Test Method herein. The bonds for each of the permanent bonds and the releasable bonds may have a bond size of 0.5 mm to 10 mm or from about 0.7 mm to 3 mm in one or more directions, according to the Bond Dimension Test Method. The permanent bonds may be larger in size than the releasable bonds. The permanent bonds and the releasable bonds may have any shape, such as rectangular, circular, hexagon, oval, diamond, or any other shape that allows the laminate to be bonded.

Referring to FIGS. 2B, the bond pattern 200 may be a plurality of bonds 30 arranged in a grid configuration. As illustrated in FIG. 2C, the bond pattern 200 may be a plurality of bonds arranged in an offset configuration such that rows of bonds are offset from adjacent rows of bonds. It is to be appreciated that the bond patterns may be irregular patterns and the density of the bonds within the bond pattern may change in various areas of the laminate. Further, the plurality of bonds may not from a bond pattern and, rather, may be non-uniformly spaced over the laminate.

Further to the above, the bond pattern 200 may include a plurality of discrete primary bonds 30, also referred to herein as permanent bonds, and a plurality of secondary bonds 32, also referred to herein as releasable bonds. The primary ultrasonic bonds may be such that the laminate 10 is permanently attached in the areas of the primary bonds 30. The secondary bonds 32 may be such that these bonds release, allowing two or more layers of the laminate to separate, when the laminate is extended in a stretch direction. The primary bonds 30 may be permanent bonds 34 and the secondary bonds may be releasable bonds 36. The releasable bonds 36 are configured to bond together two or more layers of the laminate 10 prior to the bond being released. Upon release of the releasable bond 36, two or more layers of the laminate separate, partially or fully. The releasable bond 36 may be configured to release when the laminate is extended in one or more directions. For example, the laminate may be an elastic ear. Prior to the elastic ear being stretched, the releasable bonds attach each layer of the elastic ear. Upon extension of the elastic ear, the releasable bonds 36 are released allowing two or more layers of the laminate of the elastic ear to separate. The releasable bonds 36 allow the laminate to be in relatively flat state prior to stretching and to then become relatively lofty and pillow-like upon extending and release of the releasable bonds. The permanent bonds 34 prevent the laminate from separating when the laminate is extended. The permanent bonds and the releasable bonds may both be ultrasonic bonds. The permanent bonds and the releasable bonds may be different types of bonds.

These and other features will be described in more detail below. An ear 130 and/or a waistband 180 and/or a leg cuff of an absorbent article may include a laminate as described herein.

Laminate

As noted, the laminate 10 includes one or more coverstock layers 12, 16 and an elastomeric layer 14. Coverstock layer materials may be selected from nonwovens, films and/or any other type of web-based material. In various embodiments, one or more coverstock layers include a nonwoven. Any suitable nonwoven may be used in the laminate 10. Suitable nonwovens may have a basis weight of at least about 8 gsm or at least about 10 gsm or at least about 15 gsm, or about 40 gsm or less, or about 30 gsm or less, or about 22 gsm or less, or about 17 gsm or less, or from about 10 gsm to about 22 gsm. Suitable nonwovens include but are not limited to spunbond, spunlaid, meltblown, spunmelt, solvent-spun, electrospun, carded, film fibrillated, melt-film fibrillated, air-laid, dry-laid, wet-laid, hydroentangled, spunlaced, air-through bonded and other nonwoven web materials formed in part or in whole of polymer fibers, as is known in the art. In nonlimiting examples, a nonwoven includes a meltblown layer. Additionally, or alternatively, a nonwoven may include spunbond layers. In a nonlimiting example, a nonwoven includes two or more spunbond layers. In further nonlimiting examples, one or more nonwovens may include a SMS (spunbond-meltblown-spunbond) configuration. In further nonlimiting examples, one or more nonwovens may include a SPS (spunbond-pulp-spunbond) configuration. Alternatively, one or more of the nonwovens in the ear of the absorbent article may be void of meltblown layers. While meltblown layers have been found to enhance bonding in ears requiring adhesive (given the meltblown layer's inhibition of the adhesive's diffusion through the porous nonwoven structure), meltblown layers often lack strength. In some embodiments, a nonwoven consists essentially of spunbond layers. In some nonlimiting examples, both the first and the second nonwoven include at least 2 spunbond layers, or 3 or more spunbond layers. The fibers of the nonwoven may be joined by a plurality of thermal point bonds as is known in the art. In non-limiting examples, the nonwoven(s) may include a bond area (with respect to their thermal point bonds) of about 20% or less.

The nonwoven web may be formed predominately of polymeric fibers. In some examples, suitable nonwoven fiber materials may include, but are not limited to polymeric materials such as polyolefins, polyesters, polyamide, nylon, or specifically, polypropylene (PP), polyethylene (PE), poly-lactic acid (PLA), polyethylene terephthalate (PET) and/or blends thereof. In some examples, the fibers may be formed of PP/PE blends such as described in U.S. Pat. No. 5,266, 392. Nonwoven fibers may be formed of, or may include as additives or modifiers, components such as aliphatic polyesters, thermoplastic polysaccharides, or other biopolymers. Further useful nonwovens, fiber compositions, formations of fibers and nonwovens and related methods are described in U.S. Pat. Nos. 6,645,569; 6,863,933; and 7,112,621; and in U.S. patent application Ser. Nos. 10/338,603; 10/338,610; and 13/005,237. The individual fibers of a nonwoven layer may be monocomponent or multicomponent (including bicomponent). The multicomponent fibers may be bicomponent, with differing polymeric components in, e.g., a core-and-sheath or side-by-side arrangement. The individual components may include polyolefins such as polypropylene or polyethylene, or their copolymers, or polyesters, thermoplastic polysaccharides, or other biopolymers, or recycled or reclaimed polymer resin. Further, the nonwoven may include a blend of different fibers selected, for example from the types of polymeric fibers described above.

The individual fibers of the nonwoven may also include natural fibers. Natural fibers may be fibers derived from vegetative or naturally occurring sources, such as plants and/or trees. Suitable sources for this application include wood pulp, cotton, rice, wheat, bamboo, and seaweed. The fibrous webs may comprise fibers, fiber components (linters, seed hairs, trichomes, straw) or spun fiber from any of these naturally occurring sources or combinations thereof. Most common and also suitable spun fibers for this application are made from spinning wood pulp and bamboo.

The nonwoven may include a combination of plant-based fibers and synthetic fibers that are not plant-based. For example, the nonwoven can comprise both polypropylene fibers and cotton fibers; see, for example, U.S. Patent Application Publication No. U.S. 2017/0203542. The cotton content can range from about 3%, 5%, 10%, or 15% to about 50%, by weight of the nonwoven. When synthetic fibers such as polypropylene are employed, it is preferred that the polypropylene be non-phthalate catalyst polypropylene fibers.

In some examples, at least a portion of the fibers may exhibit a spiral curl which has a helical shape. According to one example, the fibers may include bicomponent fibers, which are individual fibers each including different materials, usually a first and a second polymeric material. It is believed that the use of side-by-side bi-component fibers is beneficial for imparting a spiral curl to the fibers. Examples of potentially suitable curled or "crimped" bicomponent fibers and nonwovens formed from them are described in U.S. Pat. Nos. 5,382,400; 5,418,045; 5,707,468; 6,454,989; 6,632,386; 5,622,772 and 7,291,239. For purposes herein, use of a nonwoven formed of crimped bicomponent or multicomponent fibers such as, for example, described in the patents and/or patent applications cited immediately above, may be desired as one or both nonwoven layers because they can feel particularly soft to the touch (for wearer comfort on the inside and aesthetically pleasing feel on the outside) and are generally quite pliable. In other nonlimiting examples, a nonwoven may be void of crimped fibers.

Where the laminate 10 includes more than one nonwoven, the nonwovens may have the same basis weight or different basis weights. Likewise, the nonwovens may have the same layer configuration (e.g., SSS) or different layer configurations (e.g., SMS, SPS).

The elastomeric layer 14 includes one or more elastomeric materials which provide elasticity to at least a portion of the layer 14. Nonlimiting examples of elastomeric materials include film (e.g., polyurethane films, films derived from rubber and/or other polymeric materials), an elastomeric coating applied to another substrate (e.g., a hot melt elastomer, an elastomeric adhesive, printed elastomer, or elastomer co-extruded to another substrate), elastomeric nonwovens, scrims, strands (including one or more strands), and the like. Elastomeric materials can be formed from elastomeric polymers including polymers having styrene derivatives (e.g., styrenic block copolymer materials), polyesters, polyurethanes, polyether amides, polyolefins, combinations thereof or any suitable known elastomers including but not limited to co-extruded VISTAMAXX®. Exemplary elastomers and/or elastomeric materials are disclosed in U.S. Pat. Nos. 8,618,350; 6,410,129; 7,819,853; 8,795,809; 7,806,883; 6,677,258 and U.S. Pat. Pub. No. 2009/0258210. Commercially available elastomeric materials include KRATON (styrenic block copolymer; available from the Kraton Chemical Company, Houston, TX), SEP-TON (styrenic block copolymer; available from Kuraray America, Inc., New York, NY), VECTOR (styrenic block copolymer; available from TSRC Dexco Chemical Company, Houston, TX), ESTANE (polyurethane; available from Lubrizol, Inc., Ohio), PEBAX (polyether block amide; available from Arkema Chemicals, Philadelphia, PA), HYTREL (polyester; available from DuPont, Wilmington, DE), VISTAMAXX (homopolyolefins and random copolymers, and blends of random copolymers, available from EXXON Mobile, Spring, TX), VERSIFY (homopolyolefins and random copolymers, and blends of random copolymers, available from Dow Chemical Company, Midland, Michigan), and INFUSE (Block copolymer available from Dow Chemical Company).

In nonlimiting examples, the elastomeric layer 14 includes a film 15. The film may be a single layer or multiple layers. The film may be extensible or may be elastic in the lateral direction and/or in the longitudinal direction. The film may be pre-processed, such as by pre-activating, as disclosed, for example, in U.S. Pat. No. 9,533,067. Additionally, or alternatively, the elastomeric layer 14 may be apertured.

The elastomeric layer may be shorter in one or more dimensions of the laminate than the laminate itself. For example, the elastomeric layer may comprise a maximum dimension, Y, in the stretch direction and the laminate may comprise a maximum dimension, W, in the stretch direction, such as illustrated in FIGS. 2A-2C. In various embodiments, the stretch direction is the lateral direction. The maximum dimensions are measured when the laminate is in the relaxed state. In nonlimiting examples, Y may be less than W, by at least about 10 mm. In certain embodiments, Y is at least about 20% of, or from about 25% to about 100%, or from about 35% to about 85%, or about 80% or less of W. In various embodiments, the stretch direction is the lateral direction. Additionally, or alternatively, the elastomeric layer may have a dimension that is equal to one or more dimensions of the laminate. For example, the elastomeric layer may comprise substantially the same longitudinal length of the laminate throughout the lateral width of the laminate. In some embodiments, the elastomeric layer may have a basis weight of from about 5 to about 150 gsm, or from about 10 to about 100 gsm, or less than about 150 gsm.

Turning to FIGS. 2A-2C, the laminate 10 may include a primary region 18, defined by the perimeter of the elastomeric material 14, and one or more inelastic regions 20, 22. The primary region 18 includes an elastic region 26 and one or more unstretched zones 28. In the elastic region 26, the laminate 10 is elastically extensible. In the unstretched zones 28, the laminate 10 may not be elastic despite the presence of the elastomeric layer. In some embodiments, the area of the primary region 18 includes at least about 20% of, or from about 30% to about 100%, or about 80% or less of the total area of the laminate. The laminate 10 may include one or more inelastic regions 20, 22. In certain embodiments, the laminate 10 includes a first inelastic region 20, which extends laterally outward from a first laminate edge 9 of the laminate and is adjacent to the elastic region 18 at a first elastomeric material edge 17. The laminate may include a second inelastic region 22, which may extend laterally inward from a second laminate edge 11 and may be adjacent to the elastic region 18 at a second elastomeric material edge 19. The first and second inelastic regions may be made of the same material(s) or different materials.

Figure 14:
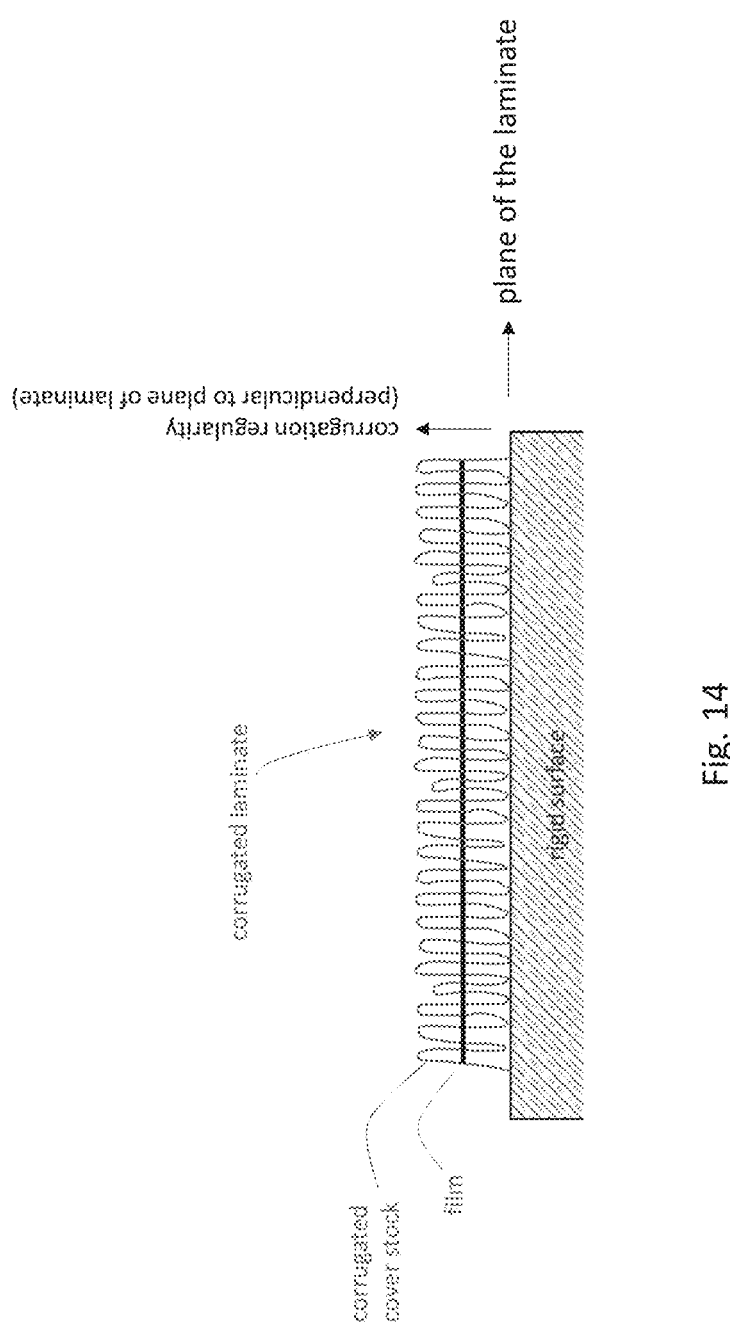
FIG. 14 is an illustration of a corrugated laminate on a rigid surface in accordance with one embodiment of the present disclosure.

In certain embodiments, the laminate 10 includes a gathered laminate 24, wherein one of the layers is strained to a greater degree than a remaining layer during lamination. In this way, the less extensible layer, such as the coverstock layer 12, 16, will form gathers when the gathered laminate 24 is in a relaxed state. In some embodiments, at least a portion of the elastomeric layer is strained while the coverstock layer, including one or more nonwovens, are in a relaxed state during lamination. The elastomeric layer may be stretched in one or more directions. Corrugations then form in the nonwoven layer(s) when the subsequently formed laminate 24 is in a relaxed state. The laminate may have a corrugation regularity of greater than about 50%, such that about 50% of the corrugations have substantially the same amplitude as measured perpendicular to the planar surface of the laminate, such as illustrated in FIG. 14. The laminate may have a corrugation regularity of greater than about 75%, such that about 75% of the corrugations have substantially the same amplitude as measured perpendicular to the planar surface of the laminate, such as illustrated in FIG. 14. When making gathered laminates, the elastomeric layer is extended in the stretch direction (i.e., the intended direction of stretch in the final product). The stretch direction may be lateral. In nonlimiting examples, the elastomeric layer is stretched in a direction corresponding with the lateral direction of the article. In other words, when the laminate is joined to the chassis subsequent to lamination, the laminate will be oriented such that the laminate is stretchable in the lateral direction of the article (i.e., the laminate is laterally-extensible).

As illustrated in FIG. 2A, for example, the laminate layers are joined by one or more bonds 30. Bonds may be any suitable shape and multiple shapes may be utilized within the laminate. In various embodiments, the bonds may be ultrasonic bonds 31. The bonds may be disposed in one or more patterns 200. Each pattern may include one or more closed cell units 204. Repeating closed cell units form one or more repeating units 202. Repeating units are the same or substantially the same closed cell units that repeat in a bond pattern. Thus, a first repeating unit includes first closed cell units having substantially the same shape and a second repeating unit includes second closed cell units having substantially the same shape; however, the first closed cell units and the second closed cell units are different shapes. It is to be appreciated that a closed cell unit of different repeating units may differ in at least one of shape and size. The bond pattern may include closed cell units where each closed cell unit is the same or substantially the same shape and/or size. The bond pattern may include closed cell units where the closed cell units are different, such as different shape and/or size. Certain closed cell units may be the same or substantially the same as certain other closed cell units in the bond pattern and certain other closed cell units may be different. For example, the bond pattern may include closed cell units having only a hexagonal shape, or the bond pattern may include a number of closed cell units having a hexagonal shape and a number of closed cell units having a triangular shape. The laminate may include a first bond pattern 200a, having one or more closed cell units 204 that may repeat. The first bond pattern may at least partially overlap the primary region 18.

Further, the bond pattern 200 may include permanent bonds 34. The permanent bonds 34 allow the laminate to remain bonded in the areas of the permanent bonds 34 while the laminate is stretched. The bond pattern 200 may also include releasable bonds 36. The permanent bonds 34 may be referred to as primary bonds 29 and the releasable bonds 36 may be referred to as secondary bonds 32. A releasable bond refers to an ultrasonic bond that is breakable (or releasable) upon being stretched. FIG. 2D is a schematic illustration of a stretch laminate 10 including an elastomeric film layer 14 sandwiched between a first cover layer 12 and a second cover layer 16. The layers are held together with a plurality of ultrasonic bonds 31. The stretch laminate 10 may be subjected to a lateral pull force in the stretch direction. FIGS. 2E-2G is a schematic illustration of the stretch laminate 10 of FIG. 2D with various types of releasable bond sites 36 after being subjected to the lateral pull force. In FIG. 2E, the releasable bond sites 36 separate from both the first cover layer 12 and the second cover layer 14 at areas of detachment 702. In FIG. 2F, the releasable bond sites 36 separate from either the first cover layer 12 or the second cover layer 14 at areas of detachment 702. In FIG. 2G, the releasable bond sites 36 separate only partially from either the first cover layer 12 or the second cover layer 14 at areas of detachment 702.

The releasable bonds 36 may be disposed within the closed cell units, as illustrated in FIG. 2A, and/or outside of the closed cell units. The releasable bonds 36 are releasable when the laminate is extended greater than about 5 mm in the stretch direction, according to the Laminate Extension Test Method. For example, the bonds release when at least one of the bonded layers in the areas of the releasable bond are separated from the one or more other layers or at least partially separated from the one or more layers in the area of the releasable bond. In some embodiments, the releasable bonds are released when the laminate is extended from about 5 mm to about 12 mm or from about 5 mm to about 10 mm or from about 5 mm to about 8 mm, according to the Laminate Extension Test Method. The permanent bonds remain bonded when the laminate is extended up to 15 mm.

The secondary, releasable bonds may release when the laminate peel force, the peel force exerted on the laminate, is greater than or equal to 0.3 N/cm, according to the Peel Force Test Method. In another embodiment, the permanent bonds may stay bonded while the releasable bonds release when the individual bond experiences a force of 0.06 N/bond or less, according to the Peel Force Test Method. In another embodiment, the permanent bonds may stay bonded while the releasable bonds release when the laminate is extended by a force of 0.5 N/in or more in the stretch direction, according to the Laminate Extension Test Method. In some embodiments, the releasable bonds of the laminate may be released when the laminate is extended by a force of about 0.4 N/in to about 0.7 N/in or from about 0.4 N/in to about 0.5 N/in, according to the Laminate Extension Test Method.

It is to be appreciated that one or more of the releasable bonds may be released prior to the 5 mm extension of the laminate in the stretch direction. For example, the secondary or releasable bonds may be configured such that one or more of releasable bonds release when the laminate is stretched by a first extension, which is less than 5 mm, in the stretch direction and a second plurality of releasable bonds release when the laminate is stretched by a second extension, which is greater than or equal to 5 mm, in the stretch direction. For example, a laminate stretched by a first extension, about 5 mm, in the stretch direction results in release of a first portion of the releasable bonds, either partially or fully, and the laminate stretched by a second extension, about 10 mm, in the stretch direction results in the release of the remainder or a second portion of the releasable bonds, either partially or fully. Similarly, one or more releasable bonds may release prior to the laminate being extended by a force of 0.5 N/in in the stretch direction while additional bonds may not be released until the laminate is extended by a force of greater than or equal to 0.5 N/in in the stretch direction. It is also to be appreciated that one or more of the releasable bonds may not be released when the individual releasable bonds experience a peel force of 0.06 N/bond or less, according to the Peel Force Test Method. Thus, as more force is exerted on the releasable bonds, additional releasable bonds may be released. For example, all releasable bonds are released when the individual releasable bonds experience a force of 1.2 N/bond or less. In a preferred embodiment, substantially all of the releasable bonds are configured to be released when the individual releasable bonds experience a force of about 0.06 N/bond or less, which is about the force exerted by a user when applying an absorbent article that includes the laminate, as disclosed herein.

The release of the releasable bonds allows the bonded region to undergo a change from a relatively compressed region to a more pillow-like region. For example, the releasable bonds or secondary bonds may be present in an ear of a disposable absorbent article and the secondary or releasable bonds may be released when the absorbent article is applied to a wearer for the first time. The release of the releasable bonds may allow for an ear with a relatively more pillow-like feel, greater breathability, and/or increased air flow to be present as the absorbent article is in-use or placed on the wearer. Further, the release of the releasable bonds may result in a change in opacity, graphic-visibility, and/or color intensity. The release of the releasable bonds may also result in increased thickness of the laminate.

To achieve a more pillow-like region, the number of primary bonds 29 is greater than the number of secondary bonds 32. Stated another way, the number of permanent bonds 34 may be greater than the number of releasable bonds. The permanent bonds 34 and the releasable bonds 36 may have a bond ratio. The bond ratio is the ratio of permanent bonds 34 to releasable bonds 36. The number of permanent bonds and releasable bonds may be determined by the Bond Ratio Test Method. The laminate has a bond ratio that is 1 or greater than about 1 or greater than about 1.1 or greater than about 1.3 or greater than about 1.5 or greater than about 1.7 or greater than about 2 or greater than about 5 or greater than about 8 or greater than about 10, according to the Bond Ratio Test Method. Having a bond ratio greater than 1 allows the laminate to remain sufficiently attached for use with the releasable bonds being separated during use. Further, the bond ratio allows the laminate to be sufficiently compressed prior to use, such as while in a packaged state, and to become relatively pillow-like while maintaining a sufficient amount of attachment between the layers during use, after extension.

As illustrated in FIG. 2A, the releasable bonds 36 may be disposed within the closed cell units, which are made up of permanent bonds 34. The releasable bonds 36 may allow for the closed cell units to maintain a more compressed state prior to use or stretching of the laminate. Upon release of the releasable bonds 36, the laminate in the area of the releasable bond 36 may be released causing the laminate in the area of the releasable bond 36 to separate such that the releasable bond 36 no longer bonds the laminate or only partially bonds the laminate, such as where one or more fibers remains bonded. Upon release of the releasable bonds, the permanent bonds are still discernable by the user.

The releasable bonds 36 may be part of a bond pattern that does not include closed cells, such as illustrated in FIGS. 2B and 2C. The secondary bonds or releasable bonds may be uniformly or non-uniformly distributed across the laminate. As illustrated in FIGS. 2A, 2B and 2C, the releasable bonds may form a secondary bond pattern across the laminate. It is to be appreciated that the first bond pattern formed by the permanent bonds may not be fully recognizable by the user until the second bond pattern formed by the releasable bonds is released. Further, the first bond pattern formed by the permanent bonds and the second bond pattern formed by the releasable bonds may form a cooperative bond pattern prior to the release of the releasable bonds and the first bond pattern may become visible upon the release of the second bond pattern.

Each of the primary and secondary bonds, which may also be referred to herein as welds, may be formed by one or methods, which include, ultrasonic bonding, adhesive bonding, mechanical bonding, such as heat and pressure or a combination of heat and pressure, and electrostatic bonding. The primary bonds may be formed by a first bonding method and the secondary bonds may be formed by a second bonding method. The first bonding method may be different from the second bonding method. In some embodiments, the primary bonds and the secondary bonds may be formed by the same bonding method but have differing bond strengths. For example, to alter the bond strength the bonds may be different sizes, include different materials, and be different shapes. Further, the bonds may be formed by the same methods but have different bond strength due to the differing structure of the nonwoven fibers, such as cross sectional area of the fibers, and/or elastic film properties or coatings.

As previously discussed, the permanent bond and the releasable bonds may form one or more bond patterns. These bond patterns may include bonds that are uniformly or non-uniformly distributed. These bond patterns may also form one or more closed cell units. Further, the permanent bonds may form a first bond pattern and the releasable bonds may form a second bond pattern. Upon release of the releasable bonds, the second bond pattern may be removed from the laminate and the first bond pattern may remain. Further still, the permanent bonds may form a first bond pattern and the releasable bonds may form a second bond pattern. Upon release of the releasable bonds, the second bond pattern may be removed from the laminate and the permanent bonds may from a third bond pattern that is different than the first bond pattern.

FIGS. 3A-5B provide examples of bond patterns having permanent bonds and releasable bonds. For example, FIGS. 3A-3C illustrate a bond pattern having a closed cell unit that includes a perimeter 206 formed by one or more permanent bonds 34 and releasable bonds 36. For example, FIGS. 3A and 3B illustrate multiple closed cell units 204 that form a first bond pattern 200 and a second bond pattern 201. The first bond pattern 200 and the second bond pattern 201 may be formed by one or more permanent bonds 34 and one or more releasable bonds 36. FIG. 3B illustrates a portion of the bond patterns illustrated in FIG. 3A and the perimeter 206 formed by each of the closed cell units. The perimeter 206 is shown as a dashed-line for illustrative purposes and to better understand the present disclosure; however, the dashed-line forms no part of the bond pattern. The perimeter 206 is formed by connecting adjacent, individual bonds. It is to be appreciated that the perimeter of a first closed cell unit may form part of the perimeter of a second closed cell unit. Further, the perimeter 206 may be formed by connecting one or more permanent bonds and releasable bonds.

Referring to FIG. 3C, upon extending the laminate in a stretch direction, the releasable bonds 36 release and leave the permanent bonds 34. The permanent bonds 34 remaining after the release of the releasable bonds 36 reveals a third bond pattern that is different than both the first bond pattern and the second bond pattern. Further, the release of the releasable bonds 36 provides for greater area of the laminate to be unrestricted by bonds, which results in a more pillow-like or cushion-like appearance of the laminate.

Closed cell units may be any shape such that it is identifiable as a shape having a perimeter that substantially surround an area. For example, closed cell units may be various shapes including polygons, hearts, circles, ellipses, and combinations thereof. The bond pattern may include closed cell units each having the same shape. The bond pattern may include closed cell units having different shapes. Some bond patterns may include more than one closed cell unit having different shapes. For example, as illustrated in FIGS. 3A and 3B, the bond pattern may include a first closed cell unit 204*a* and a second closed cell unit 204*b*. The first closed cell unit 204*a* may be a hexagon-shaped closed cell unit and the second closed cell unit 204*b* may be a triangular-shaped closed cell unit. It is also to be appreciated, that various closed cell units may be substantially the same shape but be of different sizes. The closed cell units may form a pattern, such as previously discussed.

Bond patterns with closed cell units, as discussed herein, allow for relatively larger areas of the nonwoven to gather when the laminate is in a contracted state without the risk of having uncontrolled areas of unbonded regions that could, for example, tear. Further, these bond patterns with closed cell units allow for a more cushion-like feel against the wearer's skin and, likely, would result in less pressure and skin-marking for the wearer. The bond patterns discussed herein also may allow for relatively greater breathability.

Figure 4B:
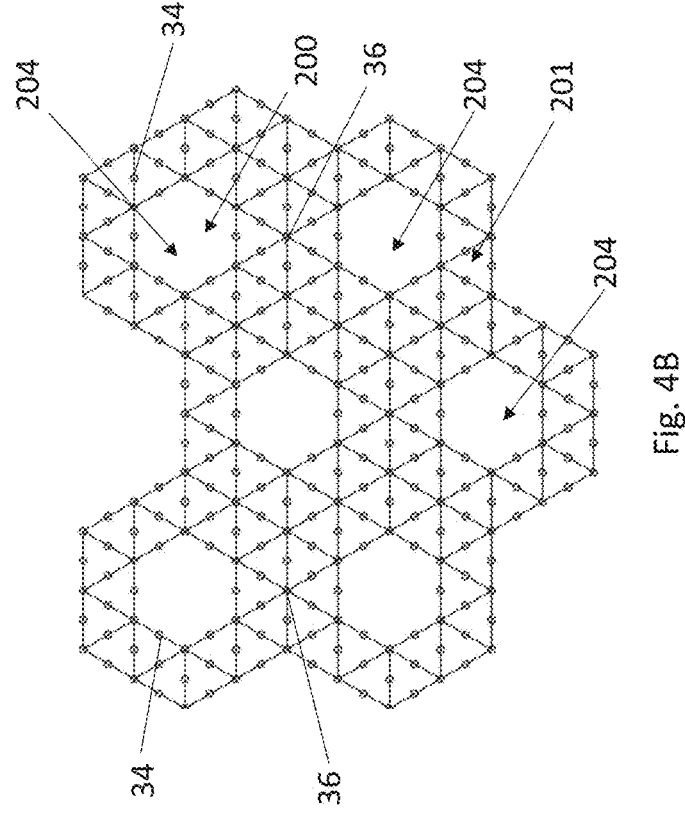
FIGS. 4A-4D are schematic representations of exemplary patterns for a laminate according to nonlimiting embodiments of the present disclosure.
Figure 4A:
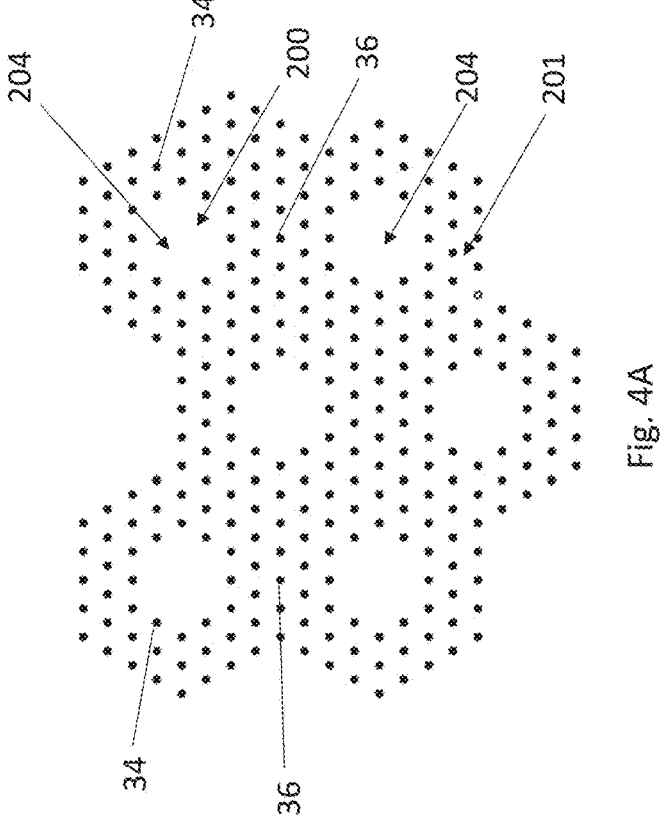
Figures 4C, 4D:
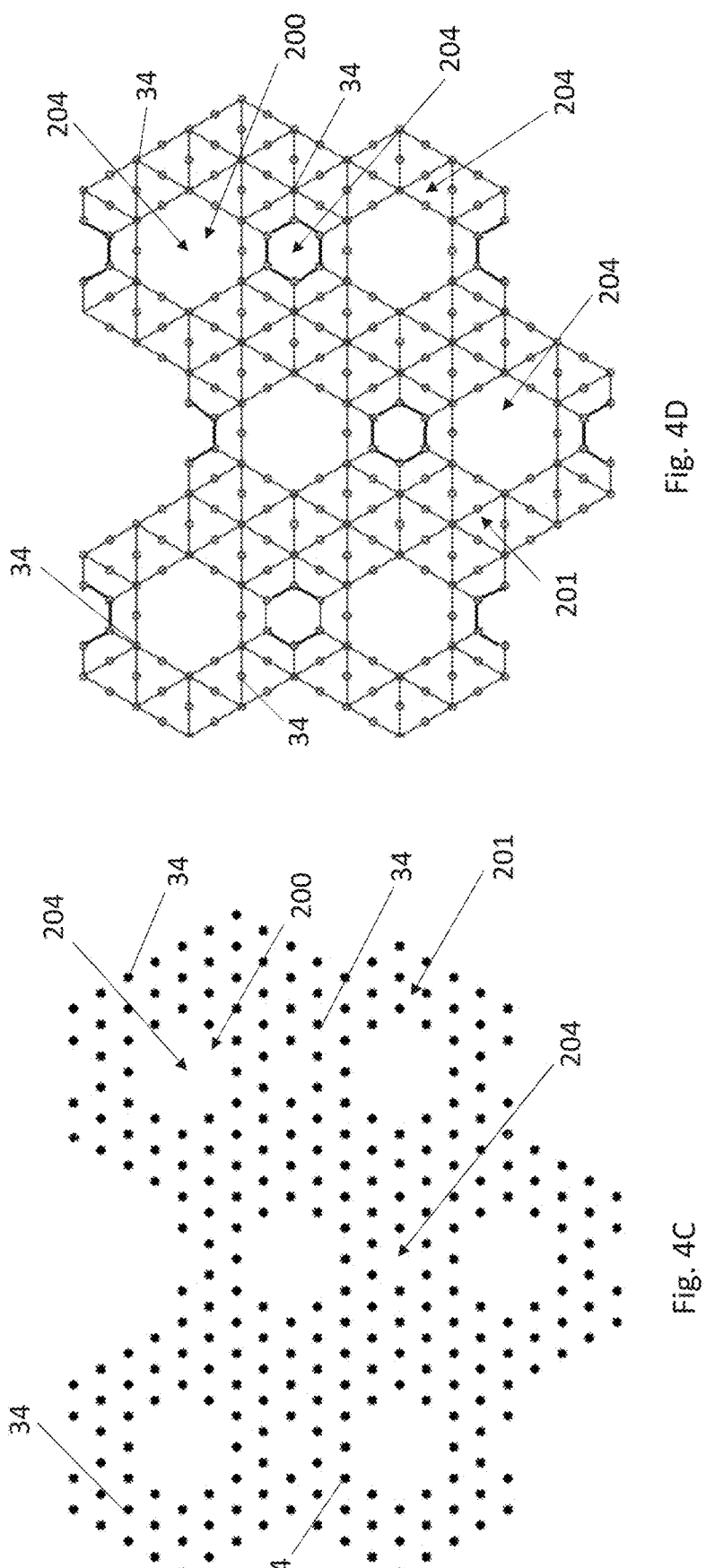

FIGS. 4A-4D illustrate another bond pattern for a laminate. The bond pattern includes both permanent bonds 34 and releasable bonds 36. FIGS. 4A and 4B illustrate the laminate, prior to extension in the stretch direction, including both the permanent bonds 34 and the releasable bonds 36 bonding the two or more layers of the laminate. The permanent bonds 34 and the releasable bonds 36 may be positioned to from closed cell units. Further, the permanent bonds 24 and the releasable bonds 36 may be positioned to from a first bond pattern 200, which forms a hexagon shaped area, and a second bond pattern 201, which forms a triangular shape. Once the laminate is extended in the stretch direction, the releasable bonds 36 may be released resulting in two or more layers of the laminate separating from one another. As illustrated in FIGS. 4C and 4D, the release of the releasable bonds result in additional closed cell units of the laminate becoming present. The laminate includes a first closed cell unit of a hexagon shape of a first size and the second closed cell unit of a hexagon shape of a second size, which is different from the first size. It is to be appreciated that in some embodiments the shape of the first closed cell unit and the shape of the second closed cell unit may be the same size. Stated another way, the shape of the patterns formed by the bonds may be the same shape and different sizes.

Figure 5B:
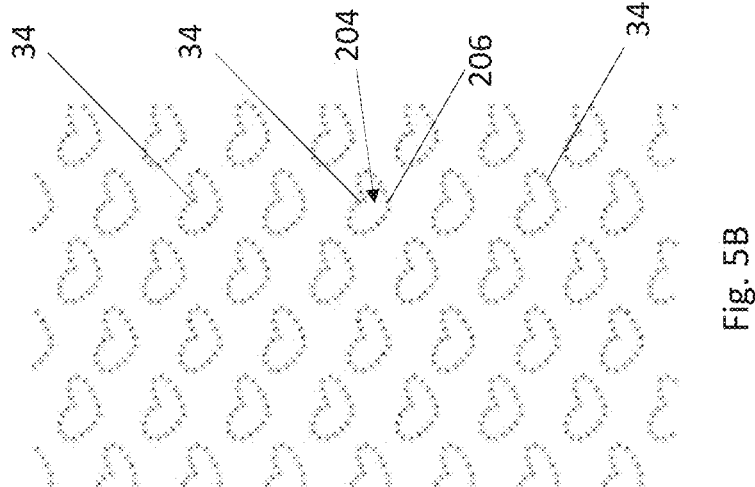
FIGS. 5A and 5B are schematic representations of exemplary patterns according to nonlimiting embodiments of the present disclosure.
Figure 5A:
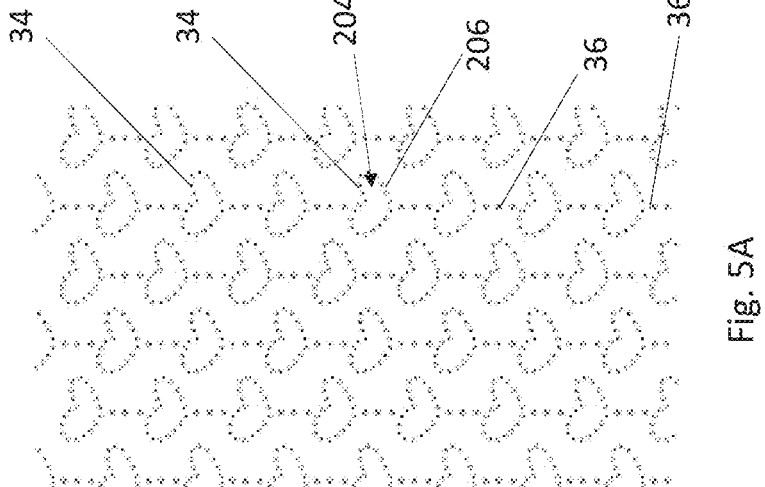

It is also contemplated that the first bond pattern may include closed cell units and areas of the bond pattern that are not enclosed. For example, as illustrated in FIG. 5A, the bond pattern may include discrete closed cell units 204. Each of the discrete closed cell units has a perimeter that does not share a perimeter of another closed cell unit. Referring to FIG. 5A, for example, the bond pattern may include closed cell units and individual bonds disposed in lines. It is also to be appreciated that the bond pattern may include one or more closed cell units that share a perimeter with one another and areas of the bond pattern that are not enclosed. The closed cell units may be formed with permanent bonds. The individual linear bonds may be formed with releasable bonds 36. Thus, when the releasable bonds are released, as illustrated in FIG. 5B, the closed cell units are independent of one another such that a bond from the first closed cell unit does not share that bond with another closed cell unit.

Figure 7:
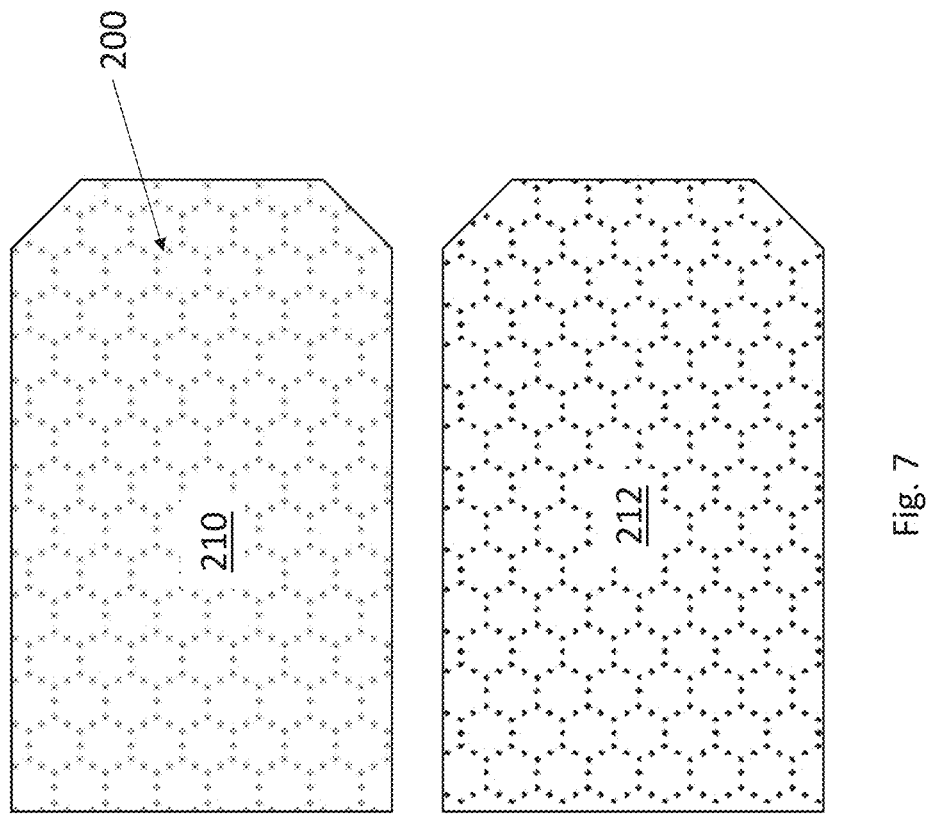
FIG. 7 is a plan view of the exterior surfaces of a laminate according to a nonlimiting embodiment of the present disclosure.
Figure 6:
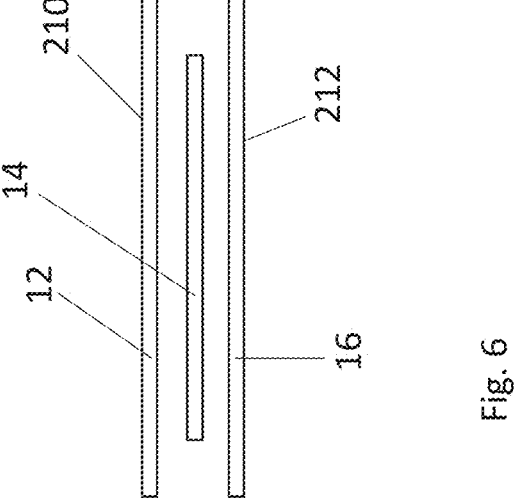
FIG. 6 is a cross-sectional view of a laminate according to a nonlimiting embodiment of the present disclosure.

In some embodiments, the laminate may have a first coverstock layer 12 including a first exterior surface 210 and a second coverstock layer 16 including a second exterior surface 212, such as illustrated in FIG. 6. The first and second coverstock layer may be made from different materials and have different basis weights, layer configurations, and extensibilities. For example, the first coverstock layer includes a nonwoven and the second coverstock layer includes a nonwoven. Alternatively, the first coverstock layer includes a first nonwoven and second coverstock layer includes a second nonwoven, such that the first and second nonwovens differ in at least one of basis weight, layer configuration (e.g., SS, SMS, SPS, etc.), and extensibility. In another nonlimiting example, the first and second coverstock layers have the same constituent material but one of the two layers includes a surface treatment or coating causing a change in the material properties such as extensibility, tensile strength, softness, or combinations thereof. In embodiments where the first and second coverstock layer differ, the same bonding pattern 200 may result in different appearance and/or different bond strength. As illustrated in FIG. 7, for example, the bonds appear relatively darker and more visually apparent on the second exterior surface 212 than the first exterior surface 210.

The area of the laminate including the bond pattern may have an Unload Force at 50% of about 0.2 N/in or greater, or about 0.3 N/in or greater, or from about 0.35 to about 1 N/in, reciting for said range every 0.01 N/in increment therein, according to the Hysteresis Test Method herein.

Figure 9:
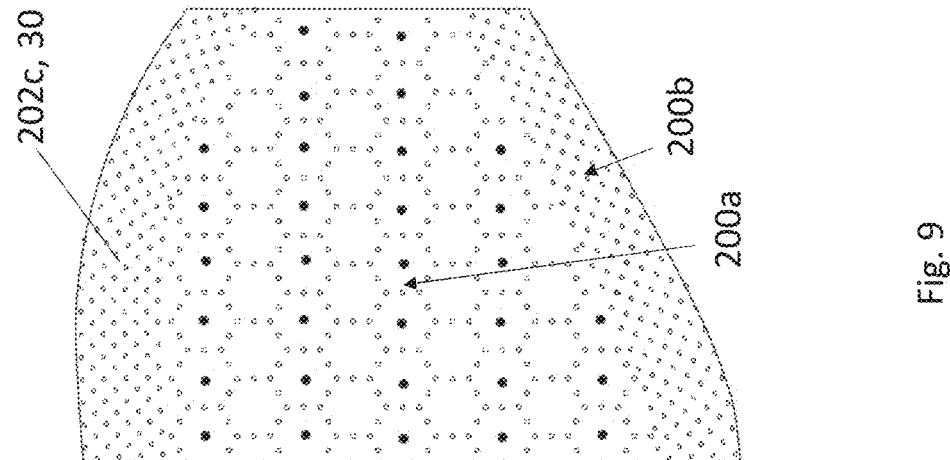
FIG. 9 is a plan view of another exemplary laminate according to a nonlimiting embodiment of the present disclosure.
Figure 8:
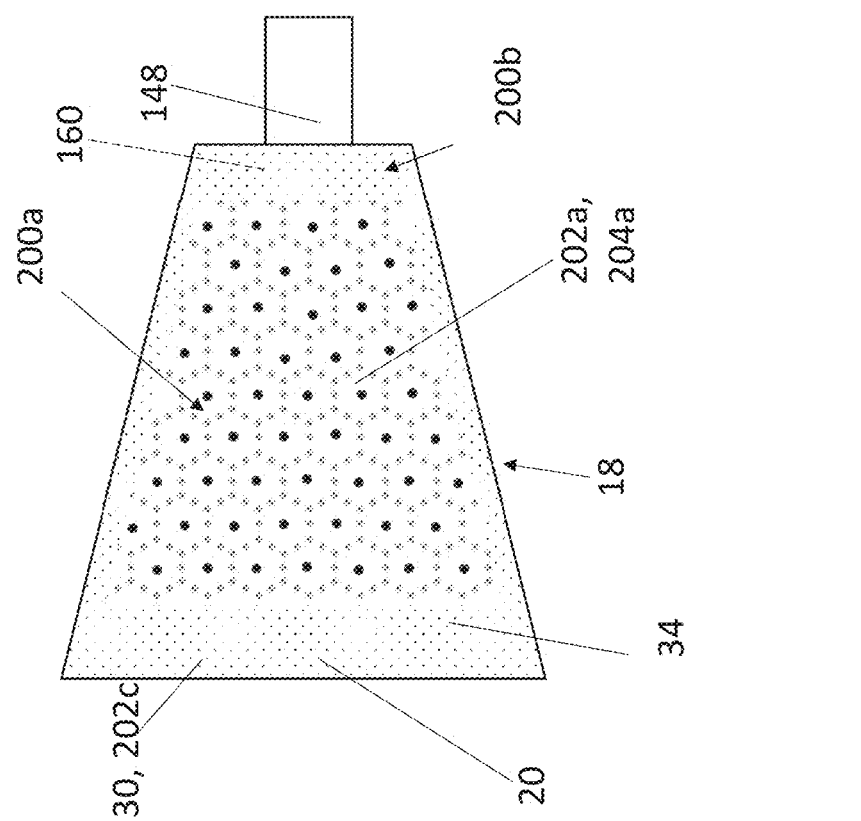
FIG. 8 is a plan view of an exemplary laminate according to a nonlimiting embodiment of the present disclosure.

The laminate may include a first bond pattern 200a and a second bond pattern 200b, as illustrated, for example, in FIGS. 8 and 9. The second bond pattern differs from the first bond pattern in at least one of shape of bonds, number of bonds, number of closed cell units (or absence of closed cell units), shape of repeat unit, enclosed area of closed cell units, bond density, bond area, and combinations thereof. The second bond pattern may be positioned outside of the first bond pattern, such that the two patterns may be in non-overlapping relationship. Such as illustrated in FIGS. 8 and 9, the second bond pattern may be disposed along one or more edges of the laminate. In this way, the second bond pattern may at least partially surround or frame at least a portion of the first bond pattern or the entire first bond pattern. The second bond pattern may at least partially overlap an unstretched region 34, an inelastic region 20, a fastening system 148, and/or reinforcement layers 160 (e.g., a folded substrate or additional substrate added to the laminate for enhanced integrity).

The first bond pattern and the second bond pattern may overlap in a transition zone. The overlap of the first bond pattern and the second bond pattern in the transition zone may be less than about 5 mm or less than about 3 mm or less than about 1 mm.

The bond patterns may include one or more releasable bonds and one or more permanent bonds. As illustrated in FIGS. 8 and 9, the first bond pattern 200a includes releasable bonds 36 and permanent bonds 34. The releasable bonds 34 may be disposed within the closed cell unit of the first bond pattern 200a. The second bond pattern 200b may also include at least one of permanent bonds 34 and releasable bonds 36 in a grid-like pattern.

The second bond pattern 200b may be void of closed cell units. Alternatively, the second bond pattern may include one or more closed cell units having any of the features described herein.

In certain embodiments, the laminate may have a Breathability Value of at least about 1 $m^3/m^2/min$, or from about 1 $m^3/m^2/min$ to about 125 $m^3/m^2/min$, or from about 2 $m^3/m^2/min$ to about 50 $m^3/m^2/min$, according to the Air Permeability Test Method herein.

Bond pattern of the laminate may coordinate with other portions of the absorbent article. For example, the bond pattern of the laminate may coordinate with a bond pattern on the chassis, such as the topsheet and/or the backsheet, the ears, the fasteners, and/or the waist feature. The coordinating pattern may be a pattern formed by mechanically changing the structure of the material or adding materials to from a pattern, such as by printing. The bond pattern of the laminate may coordinate with a bond pattern included on another portion of the absorbent article, such that the bond patterns are the same or the bond patterns may differ, for example, in terms of size, such that one bond pattern is larger or smaller than the other bond pattern. The bond patterns may coordinate such that the bond patterns have the same geometric shape.

The laminate may include added materials such as inks, color-changing indicators, and skin compositions, such as moisturizers, fragrances, lubricants, anti-bacterial substances, bug repellency substances, and UV-protection substances. The added materials may be disposed on one or more layers of the laminate. The added materials may be disposed on the surface of the one or more layers of the laminate. For example, inks may be applied to the laminate by printing. The ink may provide a visual signal to the user, such as the location of the releasable bonds or the bond pattern or a graphic.

Various methods may be used to manufacture the laminate, as previously described. For example, a method for manufacturing an elastic laminate may include the following steps. A first substrate and a second substrate may be provided. The first substrate and the second substrate may be any material as previously discussed, such as a nonwoven. The first substrate and the second substrate may each include a first surface and an opposing second surface and define a width in a cross direction. The first surface of the first substrate may be wrapped onto an outer circumferential surface of an anvil. An elastic film or other elastomeric substrate may be advanced in a machine direction.

The elastic film may be preactivated in the machine direction, a cross direction, which is substantially perpendicular to the machine direction, or both. For the pre-activation process, the elastomeric film may be guided through a system of intermeshing profile rollers, each roller including disk packets having a plurality of intermeshing disks that are situated on an axis. This process is commonly referred to as ring rolling process. In this case, the elastomeric film is transversely stretched by the intermeshing disk packets.

The stretching may be uniform or varied over the width of the film. The pre-activation process can be carried out at varying pitch and or varying depths of engagement. The pre-activation process can also be carried out in the machine direction, or in any other direction. Pre-activation through ring rolling creates visible lines on the film by virtue of the local mechanical deformation caused by the intermeshing disks and these lines are also known as activation stripes. The activation stripes formed on the elastic film may be visible to the naked eye.

The pre-activation of the elastomeric film has a positive effect on the stretching force profile and helps allow for an easy stretching action of the fabricated stretch laminate over a large expansion area. Further, the recovery of the stretch laminate can also be improved by pre-activating the elastomeric film. The recovery is the ability of a stretch laminate to return to original size after it has been stretched to its expansion limit. The increased recovery of elastomeric film after the pre-activation process is due to the removal of an amount of set from the film. Pre-activation of elastomeric films is disclosed in U.S. patent Ser. No. 11/135,100, which is incorporated by reference.

Elastomeric films may also include at least one skin disposed on the elastically extensible material, the skin forming at least one of the film's surfaces. Such skin is an extensible material and provides an outer surface to elastomeric film that has less tackiness than the underlying elastically extensible material. In some embodiments, the skin may also qualify as an elastically extensible material, but will be less elastic than the underlying elastically extensible material. Accordingly, when compared to the elastically extensible material, the skin will have less recovery from the same amount of extension. Stated another way, when compared to the elastically extensible material, the skin will have a higher percentage set from the same percentage strain. The skin may aid in elastomeric film processability and is between about 1 um and about 10 um, or between about 3 um and about 7 um, or in some embodiments, is about 5 um, in thickness. In certain embodiments, the skin that overlays the elastically extensible material in elastomeric film is a polyolefin. Non-limiting examples of useful skin materials include metallocene polyethylene, low density polyethylene, high density polyethylene, linear low density polyethylene, very low density polyethylene, a polypropylene homopolymer, a plastic random polyropyl ene/olefin) copolymer, syndiotactic polypropylene, metallocene polypropylene, polybutene, an impact copolymer, a polyolefin wax, and combinations thereof. Exemplary elastomeric films that are useful in the stretch 5 laminates detailed herein (i.e., an elastically extensible material with at least one skin disposed on the surface of the elastically extensible material) include M18-1117 and M18-1361 elastomeric films commercially available from Clopay Corporation of Cincinnati, Ohio; K11-815 and CEX-826 10 elastomeric films commercially available from Tredegar Film Products of Richmond, Va.; and elastomeric films commercially available from Mondi Gronau GmbH of Gronau, Germany. These exemplary elastomeric films include a single layer of elastically extensible material with 15 um skin disposed on both surfaces of the material.

Films suitable for this application would have a skin providing first surface and a second skin providing second surface. During pre-activation, the skin and the elastically extensible material are similarly stretched (i.e., put under similar strain). However, after stretching, the skin and the elastically extensible material will retract and recover differently (i.e., have different set values). In comparison with the elastically extensible material, the skin is less elastic and therefore will have less recovery after stretching, a.k.a., a higher set value. The skin is also much thinner than the elastically extensible material, so when the thicker elastically extensible material retracts and recovers after pre-activation stretching, it will force the attached skin to retract with it. But because the skin cannot recover as much as the elastically extensible material, the skin buckles and wrinkles. Without pre-activation, the skins, and thus the outer surfaces of the elastomeric film, are substantially smooth in a cross-sectional view. With pre-activation, the skins and thus the outer surfaces of the elastomeric film, are substantially wrinkled in a cross-sectional view, such as disclosed in U.S. Pat. No. 10,485,713, which is incorporated by reference.

The preactivated elastic film may be advanced to a spreader mechanism, which includes an engagement portion. The elastic film may be stretched at the spreader mechanism in the cross direction or machine direction to a first elongation. The elastic film is then advanced from the spreader mechanism to the anvil. The anvil may include an active vacuum zone having a maximum width in the cross direction. The elastic film is positioned in contact with the second surface of the first substrate on the anvil, and the second substrate is advanced to position the first surface of the second substrate in contact with the elastic film and the second surface of the first substrate on the anvil. The first substrate together with the second substrate with the elastic material positioned between the first substrate and the second substrate are ultrasonically bonding. A sonotrode may be used to ultrasonically bond the laminate. The ultrasonic bonding of the laminate imparts one or more bond patterns such as previously discussed herein. Methods of manufacturing laminates are disclosed in the commonly owned publications, which are incorporated herein by reference: U.S. Pat. Nos. 10,561,537; 10,568,776; U.S. Pat. Pub. No. 2021/0401638; and U.S. application Ser. No. 17/493,098 filed Oct. 4, 2021.

Releasable bonds may be created through a variety of means, including reduction of bond size, reduction of bond pressure, reduction of bond nub height, reduction of energy transfer through nub shape or geometry. Bond nub height changes may be achieved through laser metal deposition, such as disclosed in U.S. Pat. Pub. No. 2020/0180025.

Article Including a Laminate

Figure 10:
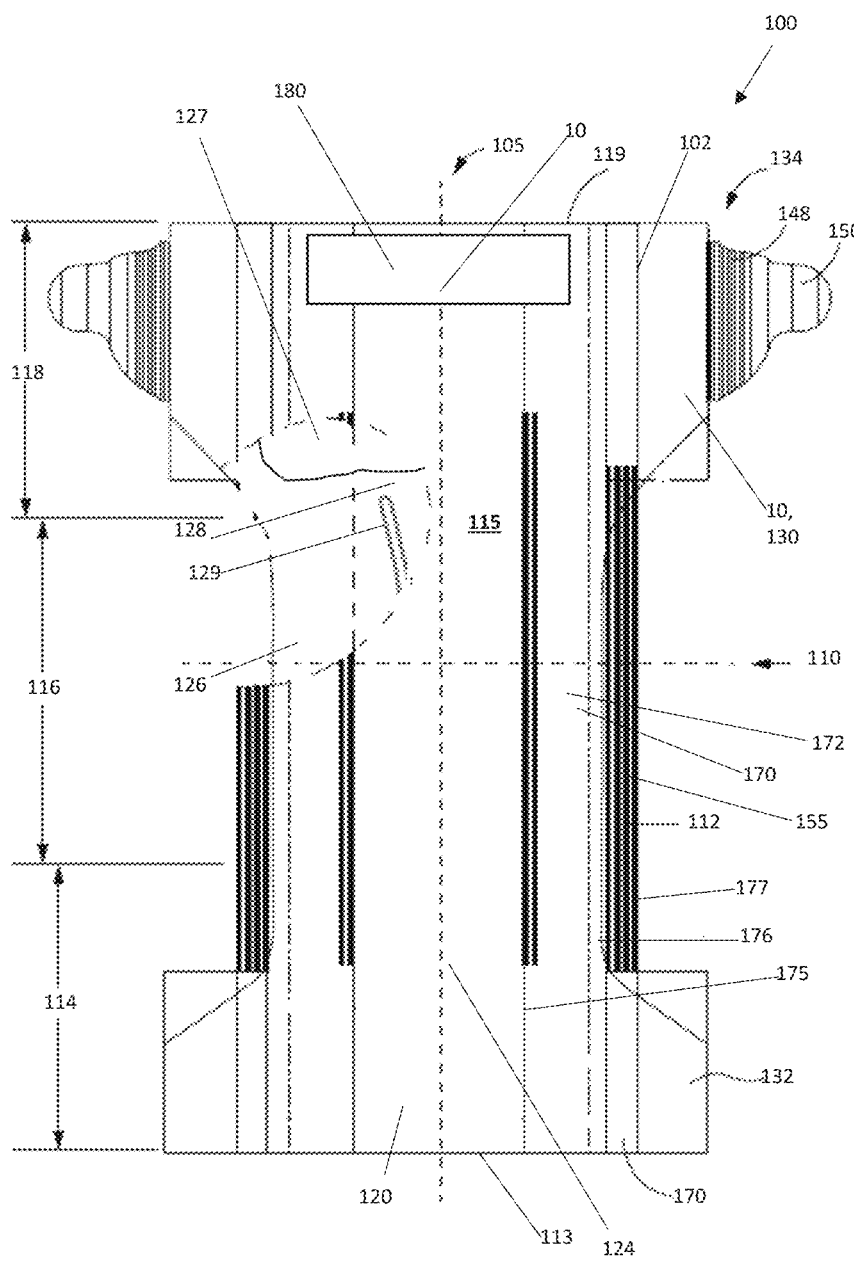
FIG. 10 is schematic plan view of an exemplary absorbent article according to one nonlimiting embodiment of the present disclosure. The absorbent article is shown in a flat, uncontracted state.

With reference to FIG. 10, a laminate 10 of the present disclosure may be incorporated into an absorbent article 100, such as a disposable absorbent article. The laminate may be attached to one or more layers of the chassis 120 by a chassis attachment bond 102. The chassis attachment bond may include ultrasonic bonds, adhesive bonds, mechanical bonds, or combinations thereof.

FIG. 10 is a plan view of an exemplary, non-limiting embodiment of an absorbent article 100 in a flat, uncontracted state. The body-facing surface 115 of the absorbent article 100 is facing the viewer. The absorbent article 100 includes a longitudinal centerline 105 and a lateral centerline 110.

The absorbent article 100 includes a chassis 120. The absorbent article 100 and chassis 120 are shown to have a first waist region 114, a second waist region 118 opposed to the first waist region 114, and a crotch region 116 located between the first waist region 114 and the second waist region 118. The waist regions 114 and 118 generally include those portions of the absorbent article which, when worn, encircle the waist of the wearer. The waist regions 114 and 118 may include elastic members 155 such that they gather about the waist of the wearer to provide improved fit and containment. The crotch region 116 is the portion of the absorbent article which, when the absorbent article is worn, is generally positioned between the legs of the wearer.

The outer periphery of the chassis 120 is defined by longitudinal edges 112 and waist edges (first waist edge 113 in first waist region 114 and second waist edge 119 in second waist region 118). The chassis 120 may have opposing longitudinal edges 112 that are oriented generally parallel to the longitudinal centerline 105. However, for better fit, longitudinal edges 112 may be curved or angled to produce, for example, an "hourglass" shape article when viewed in a plan view as shown in FIG. 10. The chassis 120 may have opposing lateral edges 113, 119 (i.e., the first waist edge 113 and second waist edge 119) that are oriented generally parallel to the lateral centerline 110.

The chassis 120 may include a liquid permeable topsheet 124, a backsheet 126, and an absorbent core 128 between the topsheet 124 and the backsheet 126. The topsheet 124 may be joined to the core 128 and/or the backsheet 126. The backsheet 126 may be joined to the core 128 and/or the topsheet 124. It should be recognized that other structures, elements, or substrates may be positioned between the core 128 and the topsheet 124 and/or backsheet 126. In some embodiments, an acquisition-distribution system 127 is disposed between the topsheet 126 and the absorbent core 128.

In certain embodiments, the chassis 120 includes the main structure of the absorbent article 100 with other features added to form the composite absorbent article structure. While the topsheet 124, the backsheet 126, and the absorbent core 128 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

Components of the disposable absorbent article can at least partially include bio-sourced content as described in U.S. Pat. Pub. Nos. 2007/0219521A1, 2011/0139658A1, 2011/0139657A1, 2011/0152812A1, and 2011/0139659A1. These components include, but are not limited to, topsheets, backsheet films, backsheet nonwovens, ears/ear laminates, leg gasketing systems, superabsorbent, acquisition layers, core wrap materials, adhesives, fastener systems, and landing zones. In at least one embodiment, a disposable absorbent article component includes a bio-based content value from about 10% to about 100%, or from about 25% to about 75%, or from about 50% to about 60% using ASTM D6866-10, method B. In order to apply the methodology of ASTM D6866-10 to determine the bio-based content of any component, a representative sample of the component must be obtained for testing. In at least one embodiment, the disposable absorbent article component can be ground into particulates less than about 20 mesh using known grinding methods (e.g., WILEY® mill), and a representative sample of suitable mass taken from the randomly mixed particles.

The laminate 10 of the present disclosure may form or be a portion of one or more components of the article, including but not limited to the ear, waist features, belts, and combinations thereof.

Topsheet

The topsheet 124 is generally a portion of the absorbent article 100 that may be positioned at least in partial contact or close proximity to a wearer. Suitable topsheets 124 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 124 is generally supple, soft feeling, and non-irritating to a wearer's skin. Generally, at least a portion of the topsheet 124 is liquid pervious, permitting liquid to readily penetrate through the thickness of the topsheet 124. The topsheet 124 may be apertured. The topsheet may be apertured by overbonding a material and then rupturing the overbonds through ring rolling, such as disclosed in U.S. Pat. No. 5,628,097.

Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

Absorbent Core

The absorbent core 128 may include a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified, or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core.

The absorbent material may be deposited as an absorbent layer having a generally rectangular outline. The absorbent material layer may also have a non-rectangular perimeter ("shaped" core), in particular, the absorbent material may define a tapering along its width towards the central region of the core (or "dog-bone" shape). In this way, the absorbent material deposition area may have a relatively narrow width in an area of the core intended to be placed in the crotch region of the absorbent article. This may provide for example better wearing comfort. Other shapes can also be used such as a "T" or "Y" or "hourglass" for the area of the absorbent material.

In some embodiments, the absorbent core may include one or more channels 129, wherein said channels are substantially free of absorbent particulate polymer material. The channels 129 may extend longitudinally or laterally. The absorbent core may further include two or more channels. The channels may be straight, curvilinear, angled or any workable combination thereof. In nonlimiting examples, two channels are symmetrically disposed about the longitudinal axis.

Backsheet

The backsheet 126 is generally positioned such that it may be at least a portion of the garment-facing surface of the absorbent article 100. The backsheet 126 may be joined to portions of the topsheet 124, the absorbent core 128, and/or any other layers of the absorbent article by any attachment methods known to those of skill in the art. Backsheet 126 may be designed to prevent the exudates absorbed by and contained within the absorbent article 100 from soiling articles that may contact the absorbent article 100, such as bed sheets and undergarments. In certain embodiments, the backsheet 126 is substantially water-impermeable. The backsheet may, for example, be or include a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Backsheet 126 may also consist of more than one layer. The backsheet 126 may include an outer cover and an inner layer. The outer cover material 40 may include a bond pattern, apertures, and/or three-dimensional features. The outer cover material 40 may be a nonwoven material, such as a hydroentangled nonwoven material. The inner layer may be made of a substantially liquid-impermeable film, such as a polymeric film. The outer cover and an inner layer may be joined together by adhesive or any other suitable material or method.

Ears/Fasteners

The absorbent article 100 may include one or more ears 130, including for example front ears 132 disposed in the first waist region and/or back ears 134 disposed in the second waist region. The ears 130 may be integral with the chassis or discrete elements joined to the chassis 120 at a chassis attachment bond 102, which may join one or more layers of the ear to the chassis. It is to be appreciated that the front ears 132 and the back ears 134 may be attached to different layers of the chassis. The ears 130 may be extensible or elastic. The ears 130 may be formed from one or more nonwoven webs, woven webs, knitted fabrics, polymeric and elastomeric films, apertured films, sponges, foams, scrims, or combinations and/or laminates of any the foregoing.

In some embodiments, the ear 130 may include elastomers, such that the ear is stretchable or extendable. In certain embodiments, the ears 130 may be formed of a stretch laminate such as a nonwoven/elastomeric material laminate or a nonwoven/elastomeric material/nonwoven laminate, which also results in the ear being stretchable. The ear 120 may be extensible in the lateral direction of the article. In some embodiments, the ear is elastic in the lateral direction. In further embodiments, the ear 130 may extend more in the lateral direction than in the longitudinal direction. Alternatively, the ear may extend more in the longitudinal direction than in the lateral direction. In certain nonlimiting examples, the ear may include one or more inelastic regions along with a separate elastic region.

In some embodiments, the ear includes a laminate of one or more nonwovens and one or more elastic materials, such as the laminate 10 having any of the features or laminate layers described herein.

Any suitable nonwoven may be used in an ear 130. Suitable nonwovens may have a basis weight of at least about 8 gsm, or less than about 30 gsm, or about 17 gsm or less, or from about gsm to about 17 gsm. Typically, lower basis weight nonwovens reduce an ear's overall strength. However, ears designed according to the principles herein can obtain high strength despite lower basis weight nonwovens. Where the ear 130 includes more than one nonwoven, the nonwovens may have the same basis weight or different basis weights. Likewise, the nonwovens may have the same layer structure or different layer structures. Further, a nonwoven in the ear may have the same or different features of nonwovens in the backsheet, topsheet, leg gasketing system and/or waist feature.

The ear may be an ultrasonically bonded ear as is disclosed for example in U.S. patent application Ser. No. 15/674,559. The ear may be a gathered laminate 24. Alternatively, the ear may be activated by processes disclosed in U.S. Pat. Pub. No. 2013/0082418, U.S. Pat. Nos. 5,167,897; 5,993,432; 5,156,793; 5,167,897; 7,062,983 and 6,843,134 for example.

The ear may be joined to the chassis at a chassis attachment bond 102. In some nonlimiting examples, the chassis attachment bond is located in an inelastic region of the ear.

The absorbent article 100 may also include a fastening system 148. When fastened, the fastening system 148 interconnects the first waist region 116 and the rear waist region 118 resulting in a waist circumference that may encircle the wearer during wear of the absorbent article 100. The fastening system 148 may include a fastening elements 150 such as tape tabs, hook and loop fastening components, interlocking fasteners such as tabs & slots, buckles, buttons, snaps, and/or hermaphroditic fastening components, although any other known fastening means are generally acceptable. The absorbent article may include a landing zone to which a fastening element can engage and/or a release tape that protects the fastening elements from insult prior to use. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. In some embodiments, the fastening system 148 and/or the element 150 is foldable.

The fastening system 148 may be joined to any suitable portion of the article 100 by any suitable means. The fastening system may be joined to the ear between layers.

Leg Gasketing System

The absorbent article 100 may include a leg gasketing system 170 attached to the chassis 120, which may include one or more cuffs. The leg gasketing system may include a pair of barrier leg cuffs 172. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximal edge joined directly or indirectly to the topsheet 124 and/or the backsheet 126 and a free terminal edge 175, which is intended to contact and form a seal with the wearer's skin. In some embodiments, the free terminal edge 175 includes a folded edge. The barrier leg cuffs 172 extend at least partially between the front waist edge 113 and the rear waist edge 119 of the absorbent article on opposite sides of the longitudinal centerline 105 and are at least present in the crotch region. The barrier leg cuffs may be joined at the proximal edge with the chassis of the article by a bond which may be made by gluing, fusion bonding, or a combination of other suitable bonding processes.

The barrier leg cuffs may be integral with the topsheet 124 or the backsheet 126 or may be a separate material joined to the article's chassis. Each barrier leg cuff 172 may include one, two or more elastic elements 155 close to the free terminal edge 175 to provide a better seal.

In addition to the barrier leg cuffs 172, the article may include gasketing cuffs 176, which are joined to the chassis of the absorbent article, in particular to the topsheet 124 and/or the backsheet 126 and are placed externally relative to the barrier leg cuffs 172. The gasketing cuffs 176 may provide a better seal around the thighs of the wearer. A gasketing cuff may include a proximal edge and a free terminal edge 177. The free terminal edge 177 may include a folded edge. Each gasketing cuff may include one or more elastic elements 155 in the chassis of the absorbent article between the topsheet 124 and backsheet 126 in the area of the leg openings. All, or a portion of, the barrier leg cuffs and/or gasketing cuffs may be treated with a lotion or another skin care composition.

In further embodiments, the leg gasketing system includes barrier leg cuffs that are integral with gasketing cuffs. Suitable leg gasketing systems which may be part of the absorbent article are disclosed in U.S. Pat. App. No. 62/134, 622, Ser. No. 14/077,708; U.S. Pat. Nos. 8,939,957; 3,860, 003; 7,435,243; 8,062,279.

Elastic Waist Feature

The absorbent article 100 may include at least one elastic waist feature 180 that helps to provide improved fit and containment, as shown in FIG. 10. The elastic waist feature 180 is generally intended to expand and contract to dynamically fit the wearer's waist. Elasticized waist features include waistbands, waist cuffs having pockets formed from a portion of the waist feature 180 that is unattached from the chassis 120, and waist panels designed to fit securely about the abdomen of the wearer. Nonlimiting examples of elasticized waist features are disclosed in U.S. patent application Ser. Nos. 13/490,543; 14/533,472; and 62/134,622. Waist features 180 may be joined to the chassis 120 in the first waist region 114 and/or in the second waist region 118. The waist feature can be used in conjunction with the ear 130 to provide desirable stretch and flexibility for proper fit of the article on the wearer. The waist feature may include a laminate 10 having any of the features described herein. The waist feature may be extensible or elastic in the lateral and/or longitudinal directions. In some embodiment, the waist feature 180 includes a belt 220. The waist feature may be attached to the chassis at a waist feature bond 182.

Adult or Baby Pant Absorbent Articles

Figure 11B:
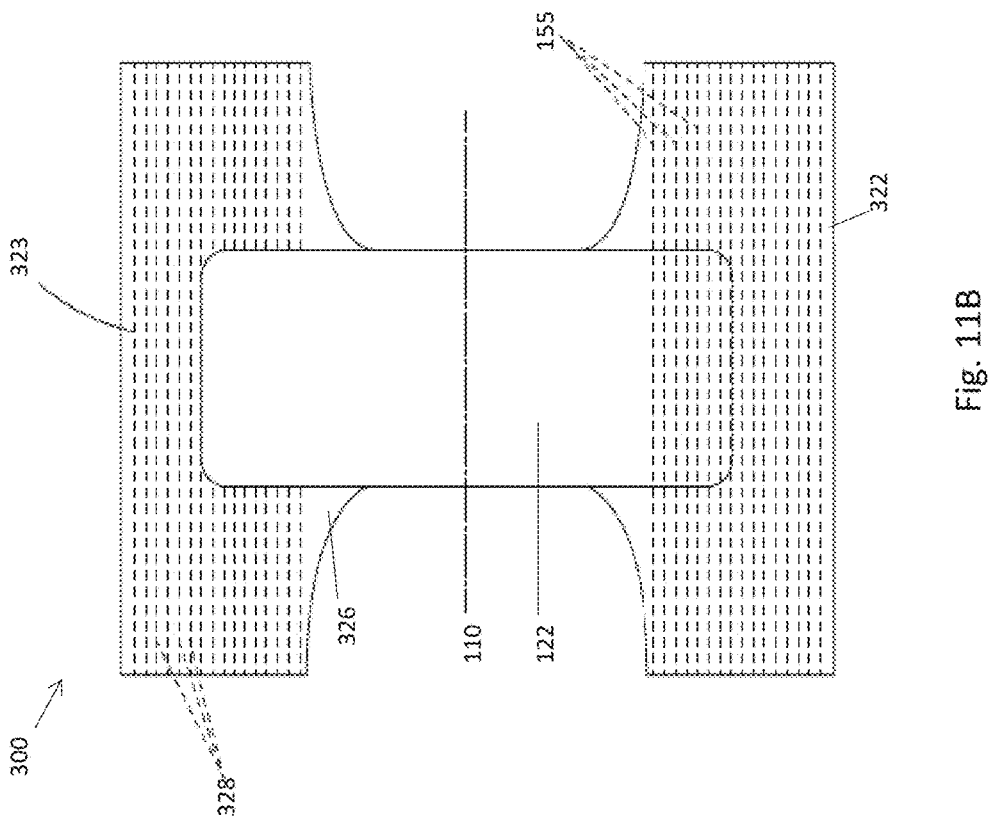
FIG. 11B is a schematic plan view of an exemplary embodiment of an absorbent pant precursor structure, prior to joining of the front and rear sections of the belt.
Figure 11A:
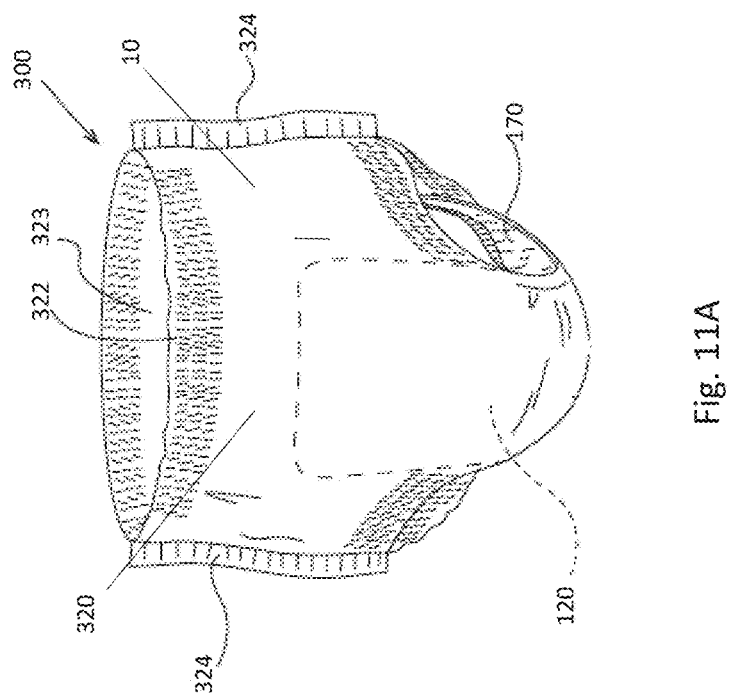
FIG. 11A is a schematic perspective view of an exemplary embodiment of an absorbent pant.

In some embodiments, the article 100 may include an absorbent pant 300 as shown in FIGS. 11A and 11B. The absorbent pant may include a chassis 120, a belt 320 to be positioned about the wearer's waist, and optionally a leg gasketing system 170. FIG. 11B depicts an exemplary precursor structure of the pant in FIG. 11A, in an open configuration laid out flat and stretched out laterally against elastic-induced contraction. In the final assembly of the pant, the front belt portion 322 is joined to rear belt portion 323 at seams 324, which may be permanent or refastenable. To form the pant 300, the precursor structure may be folded at or about lateral centerline 110 with the topsheet 124 facing inward, and the longitudinal edges of the front 322 and rear 323 belt portions may be joined at seams 324, forming a pant structure having leg openings, front waist edge and rear waist edge. In this way, the pant 300 may include a pre-formed, continuous waist opening and pre-formed, continuous leg openings for the wearer at the time of donning the pant 300.

The front and rear belt portions 322, 323 may be the outermost structures forming the front and rear regions of a pant 300. The pant may include an outer wrap 326 wrapping the entirety of the front, crotch, and rear regions, and forming an outermost pant-shaped structure. In some embodiments, the outer cover of the backsheet forms the outer wrap. An outer wrap 326 may be formed of one or more sections of nonwoven web and may be cut to a profile providing suitably tailored leg opening edge profiles as desired.

A belt 320 may include the laminate 10 of the present disclosure, having any of the afore-described features including one or more nonwoven layers and one or more elastomeric layers. The laminate layers may be joined by ultrasonic bonding.

According to some nonlimiting examples, the nonwoven used for a belt portion may include a material that provides good recovery when external pressure is applied and removed.

Elastomeric layers of waist features, such as belt portions, may include one or more elastic members 155. The elastic members 155 may be elastomeric fibers, such as LYCRA® fibers available from INVISTA of Wichita, KS, in various decitex levels. The elastic members 155 may also include any heat shrinkable elastic material as is well known in the art. Other suitable elastics can be made with various other materials including but not limited to: rubbers, styrene ethylbutylene styrene, styrene ethylene propylene styrene, styrene ethylene propylene styrene, styrene butadiene styrene, styrene isoprene styrene, polyolefin elastomers, elastomeric polyurethanes, and other elastomeric materials known in the art, and combinations thereof. In some nonlimiting examples, the elastic members may be extruded strand elastics with any number of strands (or filaments). In some embodiments, the elastic members can have a decitex ranging from 50 to 2000, or any integer value for any decitex value in this range. However, the skilled person may select the appropriate decitex based on the desired contraction and other principles discussed herein. In further embodiments, the elastic members may be in a form of film. Examples of films have been described in prior patent applications (see, for example, U.S. Pat. App. Pub. No. 2010/0040826). The film may be created with a variety of resins combined in at least one of several sublayers, the latter providing different benefits to the film.

In addition, elastic members 155 may take a multitude of configurations. For example, the width may be varied; a single strand or several parallel or non-parallel strands of elastic material may be used; or a variety of shapes may be used including rectilinear and curvilinear; or a variety of cross sectional shapes can be used (circular, rectangular, square, etc.).

Layers of a waist feature (e.g., belt portion) and/or chassis 120 may be joined together about elastic strands 155 by adhesive deposited between the layers, by thermal bonds, by compression bonds, or by a combination thereof. In other examples, the one or more elastic members may be strips or a section of film formed of elastomeric material. Where the elastic member is elongate, it may be desirable that the longer dimension be laterally oriented, or even substantially aligned with the lateral direction, as strands 155 are depicted in FIG. 11B for example.

A belt portion or other form of waist feature may include at least 3 waist elastic members, at least 5 elastic members, at least 10 waist elastic members, or at least 15 waist elastic members, or from about 2 to about 35 waist elastic members, or from about 5 to about 25 waist elastic members.

In one embodiment, adjacent elastic members 155 are spaced a longitudinal distance of at least 3.5 mm apart from one edge of the member to the other edge of the member, optionally at least 4 mm apart; optionally at least 4.5 mm apart; optionally at least 5 mm apart; optionally at least 5.5 mm apart; optionally at least 6 mm apart; optionally at least 6.5 mm apart; optionally at least 7 mm apart; optionally at least 7.5 mm apart; optionally at least 8 mm apart; optionally at least 8.5 mm apart; optionally at least 9 mm apart; optionally at least 9.5 mm apart; optionally at least 10 mm apart; optionally at least 10.5 mm apart; optionally at least 11 mm apart; optionally at least 11.5 mm apart; optionally at least 12 mm apart. The spacing between elastic members may be the same or different across the longitudinal length of the waist feature. For example, the spacing between adjacent elastic members could uniformly be 7 mm or there could be variable spacing (i.e., two adjacent elastic members are separated by 3 mm, another two are separated by 6.5 mm, etc.).

During manufacture of the waist feature, the elastic members 155 may be pre-strained by a desired amount as they are being incorporated into the waist feature. Upon subsequent relaxation of the waist feature, the elastic members will contract laterally toward their unstrained lengths. This may cause layers of the waist feature to gather and form ruffles or rugosities having ridges and valleys generally transverse to the lengths of the elastic members 155 and extending in the z-direction.

In further embodiments, to adhere the components of the waist feature laminate, the elastic members may be individually coated with adhesive ("strand coated") prior to incorporation into the waist laminate. Various coating methods and techniques, including strand coating methods and techniques, are shown for example in U.S. Pat. Nos. 5,340, 648; 5,501,756; 5,507,909; 6,077,375; 6,200,635; 6,235, 137; 6,361,634; 6,561,430; 6,520,237; 6,582,518; 6,610, 161; 6,613,146, 6,652,693, 6,719,846 and 6,737,102. The adhesive used may be a hot-melt type adhesive having elasticity and flexibility making it suitable for attaching pre-strained elastic materials to substrates, such as OMNIMELT BLOCKS 22 H2401F, or ZEROCREEP brands such as AVANCÉ, available from Bostik, Inc., Wauwatosa, Wisconsin.

In certain embodiments, corners of the front and/or rear belt portion may be trimmed off as suggested in FIG. 11B. The corners may be trimmed off along straight lines, or may be trimmed off along trim paths that are curved and either concave or convex with respect to the remaining area of the belt portion, as may be desired to impart a particular curved leg edge profile. In conjunction with such trimming and the configuration of elastic strands described above, it may be desired to impart bonding between layers along edges of the respective belt portion 322, 323. Such bonding may serve to prevent any separation of the layers along edges that may contribute to creating a ragged appearance, and may also help the rear belt portion more effectively draw inward laterally toward the central chassis 120, under the contractive force of the elastic strands below seams 324. Bonding may be effected by mechanical/compression bonds as described in, for example, U.S. Pat. Nos. 4,854,984 and 4,919,738, by thermal bonds or welds, or by deposits of adhesive between layers. In nonlimiting examples, such bonding may form a pattern along edges. Such bonding may be supplemental to any bonding between layers generally holding the respective belt portion 322, 23 together as a laminate structure.

Side seams 324 may be permanent or refastenable. Permanent seams may be formed between the front belt portion and the rear belt portion by any bonding mechanism wherein the front and rear belt portions may not be forcibly separated without substantial damage to one or both of the front and rear belt portions, or without any included mechanism by which substantial reattachment or refastening may be effected. Bonding forming permanent seams may include compression bonding, thermal bonding/welds, ultrasonic bonding, or adhesive bonding. Refastenable seams may be formed between the front belt portion and the rear belt portion by any mechanism configured to permit substantially non-destructive forcible separation of the front and rear belt portions, and subsequent substantial reattachment or refastening at the same locations. One example of such mechanism is a hook-and-loop fastening system, for example, a VELCRO fastening system. A suitably sized and shaped hooks component may be bonded to one of the front or rear belt portions along the longitudinal edges thereof, and a suitably sized and shaped loops component may be bonded to the other of the front or rear belt portions along the longitudinal edges thereof, in positions in which they may be brought together and engaged to form seams 224. Examples are depicted in U.S. Pat. App. Ser. Nos. 61/787, 416; 61/787,332; 61/666,065.

Exemplary belt and absorbent pant constructions are disclosed in U.S. patent application Ser. Nos. 14/598,783 and 14/032,595.

Package

The absorbent articles 100 of the present disclosure may be placed into packages. The packages may include polymeric films, paper, and/or other materials. Graphics and/or indicia relating to properties of the absorbent articles may be formed on, printed on, positioned on, and/or placed on outer portions of the packages. Each package may include a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

The packages may comprise polymeric films comprising recycled material, such as about 20% to about 100%, about 30% to about 90%, about 30% to about 80%, about 40% to about 60%, or about 50% recycled material. The recycled material may comprise post-industrial recycled material (PIR) and/or post-consumer recycled material (PCR). In some instances, the polymeric films used for the packages may comprise two outer layers and one or more inner layers. The one or more inner layers may comprise the recycled material or may comprise more recycled material than the outer layers. The recycled material may comprise recycled polyethylene. The recycled material may comprise recycled polyethylene PIR from trim from the packaging operation.

The package material may comprise paper, paper based material, paper with one or more barrier layers, or a paper/film laminate. The package material may be in the range of about 50 gsm to about 100 gsm or about 70 gsm to about 90 gsm and the one or more barrier layers may be in the range of about 3 gsm to about 15 gsm. The paper based package material with or without one or more barrier layers may exhibit a machine direction tensile strength of at least 5.0 kN/m, a machine direction stretch of at least 3 percent, a cross-machine direction tensile strength of at least 3 kN/m, and a cross-direction stretch at break of at least 4 percent, each as determined via ISO 1924-3.

The paper based package material or paper based package material comprising a barrier layer or film may be recyclable or recyclable in normal paper recycling operations. The recyclability extent of the paper based package may be determined via recyclable percentage. The paper based package of the present disclosure may exhibit recyclable percentages of 70 percent or greater, 80 percent or greater, or 90 percent or greater. The paper based package of the present disclosure may have a recyclable percentage of between 70 percent to about 99.9 percent, between about 80 percent to about 99.9 percent, or between about 90 percent to about 99.9 percent. In one example, the package material of the present disclosure may exhibit a recyclable percentage of from about 95 percent to about 99.9 percent, from about 97 percent to about 99.9 percent, or from about 98 percent to about 99.9 percent. The recyclable percentage of the paper based package may be determined via test PTS-RH:021/97 (Draft October 2019) under category II, as performed by Papiertechnische Stiftung located at Pirnaer Strasse 37, 01809 Heidenau, Germany. In another instance, the paper based packages of the present disclosure may exhibit an overall "pass" test outcome as determined by PTS-RH:021/97 (Draft October 2019) under category II method. Any of the paper based packages may have opening features, such as lines of perforation, and may also have handles.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, according to the In-Back Stack Height Test described herein.

Figure 12:
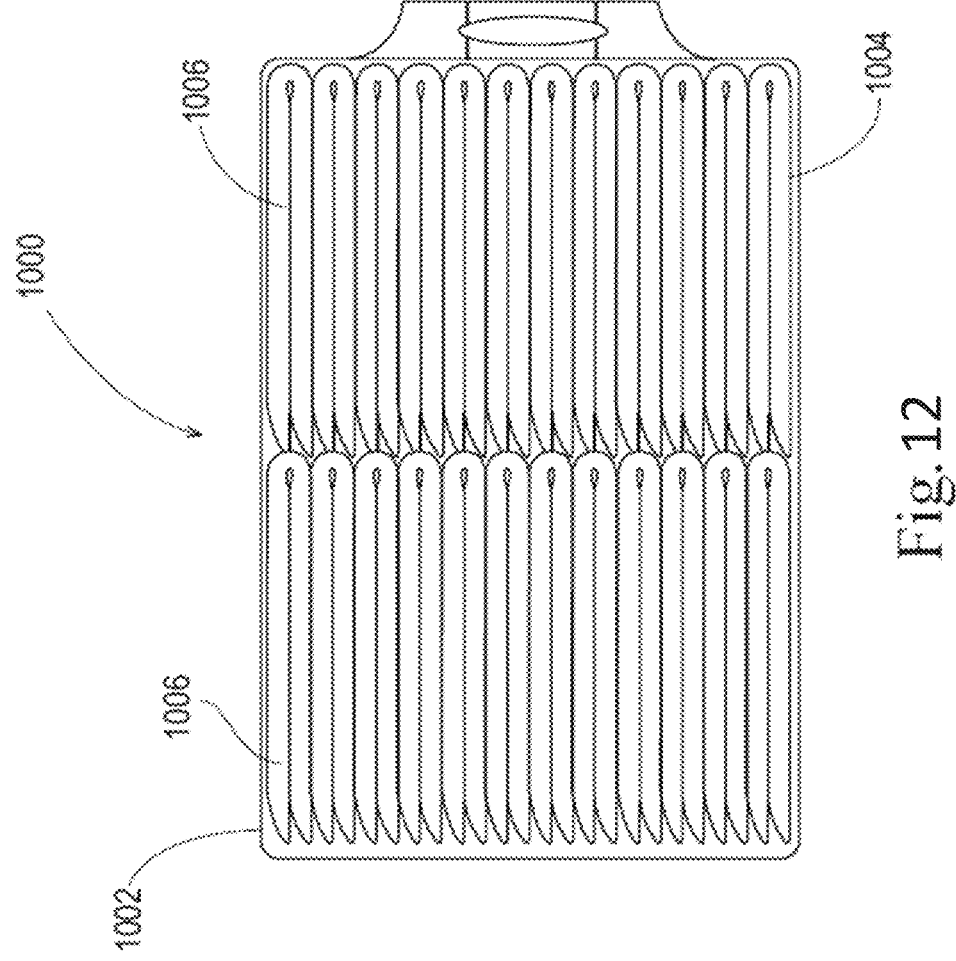
FIG. 12 is a schematic perspective view of a package in accordance with one embodiment of the present disclosure.

FIG. 12 illustrates an example package 1000 including a plurality of absorbent articles 1004. The package 1000 defines an interior space 1002 in which the plurality of absorbent articles 1004 are situated. The plurality of absorbent articles 1004 are arranged in one or more stacks 1006.

Test Methods

Bond Dimension Test Method

Figure 13:
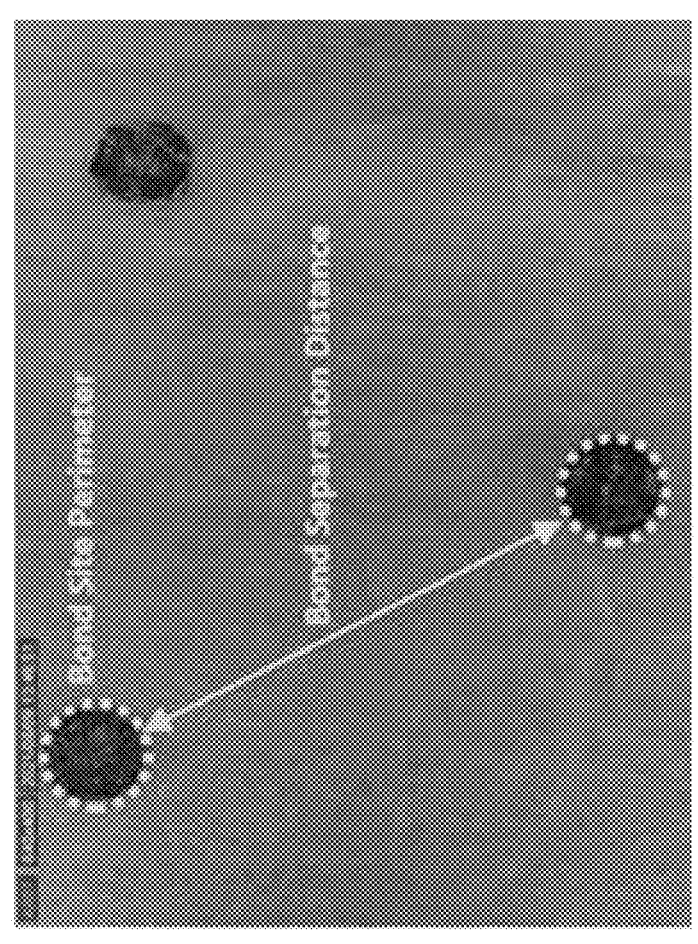
FIG. 13 is an illustration of a bond pattern in accordance with one embodiment of the present disclosure.

The Bond Dimension Test Method is used to measure various dimensions of permanent and releasable bonds in a laminate. This test measures the size of the bond (Bond Size) and the and the distance between adjacent bonds (Bond Separation Distance), such as illustrated in FIG. 13. For purposes of this method, a bond is the intentional joining of two or more layers and is the deformed area caused during the bonding process (e.g., the reduced caliper at the site of bonding or melted fibers or melted thermoplastic material). Dimensional measurements are determined from an image of a bonded laminate and obtained using an image capture tool (microscope, camera, or similar image capture tool) and image analysis software. An image of the bonded laminate is captured while the laminate is fully stretched. For corrugated laminates, the specimen is fully stretched when corrugations are substantially flattened by extending the laminate while making sure that the inelastic substrates of the laminate are not plastically deformed. For laminates without corrugations, the specimen is considered fully stretched without such extension while lying flat. Precondition samples/specimens at about 23° C.±2 C.° and about 50%±2% relative humidity for 2 hours prior to testing under the same environmental conditions.

In this method, a "unit cell" is a minimal pattern containing both permanent and releasable bonds that, when repeated through a combination of translations, reflections, and rotations, creates the entire bond pattern being interrogated. Within the image captured, a unit cell is identified, and both permanent and releasable bonds are distinguished and identified within the unit cell pattern. If permanent and releasable bonds cannot be distinguished via inspection, the Bond Ratio Test Method is used to interrogate a like unit cell to distinguish permanent bonds from releasable bonds.

Bond dimensions in the stretch direction and the longitudinal direction are measured for the selected unit area. The Bond Size in the stretch or transverse direction and the longitudinal direction, which is perpendicular to the transverse direction, are defined as the shortest (minimum) straight-line distance of the bonded area (i.e., deformed area) in the transverse direction and longitudinal direction, respectively.

For permanent bond sites, using a captured image of the unit cell, measure and record the bond size measurement in the stretch direction and measure and record the bond size measurement in the longitudinal direction. Similarly, for releasable bond sites, using a captured image of the unit cell, measure and record the bond size measurement in the stretch direction and measure and record the bond size in the longitudinal direction. This procedure is repeated for a total of 3 unit cells. Calculate and report the arithmetic mean of the recorded values and report as Bond Size for permanent bonds and releasable bonds. Report values to the nearest 0.1 mm.

The Bond Separation Distance is defined as the shortest (minimum), straight-line distance between any two individual bond sites (either permanent bond sites or releasable bond sites). As illustrated in FIG. 13, locate the perimeter of a first bond site and the perimeter of a second, different, bond site and measure the shortest straight line distance between the perimeters. Record the values and repeat for a total of 3 unit cells. Calculate and report the arithmetic mean of the recorded values and report as the Bond Separation Distance to the nearest 0.1 mm.

Peel Force Test Method

The Peel Force Test Method is used to determine the force associated with separating peel the top layer and the bottom layer of a laminate sample. A suitable tensile tester such as MTS model Alliance RT/1 with TestWorks 4® software or equivalent is used. The tensile tester is located in a temperature-controlled room at 23° C.±2° C. and 50±10% relative humidity. The instrument is calibrated according to the manufacturer's instructions. The data acquisition rate is set to at least 50 Hertz. The grips used for the test are wider than the specimen. For example, grips having 50.8 mm width may be used. The grips are air actuated grips designed to concentrate the entire gripping force along a single line perpendicular to the direction of testing stress having one flat surface and an opposing face from which protrudes a half round (radius=6 mm, e.g., part number: 56-163-827 from MTS Systems Corp.) or equivalent grips, to minimize slippage of the specimen. The load cell is selected so that the forces measured are between 5% and 95% of the capacity of the load cell used. The initial distance between the lines of gripping force (gauge length) is adjusted as required by the sample set. The load reading on the instrument is zeroed to account for the mass of the fixture and grips.

Identify a corrugated portion or stretch portion on the absorbent article product with bond patterns containing releasable, or secondary, bonds. A minimum of four specimens containing releasable bonds are collected and cut from the same portion of identical absorbent article products, such that specimens are not damaged during the separation process. The stretch direction of the specimen is the direction in which the specimen is intended to stretch in the product. Cut a specimen measuring 25 mm in the stretch direction, and at least 40 mm in the direction perpendicular to stretch direction, or as close to 40 mm as possible if at least 40 mm cannot be obtained. The specimen is delicately cut from the absorbent article from the corrugated or stretch portion of the laminate. Precondition the specimens at about 23° C.±2 C.° and about 50%±2% relative humidity for 2 hours prior to testing under the same environmental conditions. Starting at one of the ends of the specimen, peel the specimen by separating the first substrate layer from the remaining layers of the laminate at the bonded junction so as not to damage the layers, until a sufficient amount of the specimen is separated to allow mounting of the specimen in the grips. The first substrate can be a top or bottom substrate layer of the laminate. The first substrate is mounted on one of the grips and the remaining layers get mounted on the other grip.

The specimen is mounted into the grips in a manner such that there is no slack and the load measured is between 0.00 N and 0.02 N. The specimen is mounted in the center of the grips, such that the specimen peeling direction, perpendicular to stretch direction, is parallel to the applied tensile stress. The specimen is placed between the grips such that the first grip is holding the first substrate and the second grip is holding the second substrate, thereby peeling the first substrate from the second substrate in a 180° peeling direction. A skilled artisan should recognize that bonded specimens of other dimensions may be used in the Peel Force Test Method if the specimen size is smaller or larger; however, the effective bonded area should remain centered in the specimen. The peel test is initiated and the specimen is extended at 127 mm/min, with a data acquisition rate of at least 50

Hertz, until the specimens separate completely. The Peel Force in N is averaged from 5 mm after the start of crosshead travel to at least 5 mm before the end of crosshead travel, and this is reported as the Specimen Peel Force in N. The Peel Force in N is typically averaged at least over 30 mm of travel. Specimen Peel force in N/cm is calculated using following formula.

$$\text{Peel Force}\left(\frac{N}{cm}\right) = \frac{\text{Peel Force (N)}}{\text{Width of the Sample (cm)}}$$

For specimen tested as per the method prescribed dimensions, width of the specimen is 1 inch or equal to 2.54 cm.

The arithmetic mean of the Specimen Peel Force in N/cm for four specimens is recorded as the Average Peel Force (N/cm) for the either the top or bottom layer.

The peel procedure is carried for both the top layer and bottom layer of the laminate. The larger value between Average Peel Force of top layer and Average Peel Force of bottom layer is reported as Peel Force of the Laminate to the nearest 0.01 N/cm.

To calculate releasable bond peel force, cut a specimen wider in width than releasable bond width, containing only releasable bond(s), and long enough to allow for 40 mm of travel distance that the Peel Test Method as described above requires. The peel procedure is also carried out for both the top layer and bottom layer of the laminate. The smaller value between Average Peel Force of top layer and Average Peel Force of bottom layer is reported as Peel Force of the releasable bond to the nearest 0.01 N. For releasable bond peel force, the peel forced is normalized and recorded as N per average number of bonds. The number of bonds per width in specimen are calculated as follows. Draw a straight line starting from a bond site on the specimen in primary stretch direction (specimen width direction and within 5 degrees angle). Count the number of bond site(s) intersecting the line. Repeat three times, each time draw a line starting from a different bond site. Record the number of bonds intersecting each line, and record the arithmetic mean as the average number of bonds per width to the nearest 0.1 bond. The Releasable Bond Peel force is calculated using following formula:

$$\text{Release Bond Peel Force}\left(\frac{N}{bond}\right) =$$
$$\frac{\text{Peel Force (N)}}{\text{Average Number of Bonds per Width (bond)}}$$

The arithmetic mean of the Releasable Bond Peel Force in N/bond from four specimens is recorded as the Average Releasable Bond Peel Force (N/bond) to the nearest 0.01 N/bond.

Hysteresis Test Method

The Hysteresis Test Method is used to characterize purpose-specified strain or load values after being subjected to cycling of extension. The Hysteresis Test is performed using a commercial tensile tester (e.g., from Instron Engineering Corp. (Canton, MA), SINTECH-MTS Systems Corporation (Eden Prairie, MN) or equivalent). The test is performed under laboratory conditions of 23° C.±2° C. and relative humidity of 50%±2%. The specimens are conditioned for 24 hours prior to testing.

Identify a corrugated portion or stretch portion on the absorbent article product with bond patterns containing releasable bonds and permanent bonds. The specimen is cut from this area of absorbent article product to dimensions listed in the table below for the test performed.

Test Protocol

1. Select the appropriate grips and load cell. The grips must have one flat surface and must be wide enough to grasp the specimen along its full width. Also, the grips should provide adequate force and suitable surface area to ensure that the specimen does not slip during testing. The grips are air actuated grips designed to concentrate the entire gripping force along a single line perpendicular to the direction of testing stress having one flat surface and an opposing face from which protrudes a half round (radius=6 mm, e.g., part number: 56-163-827 from MTS Systems Corp.) or equivalent grips, to minimize slippage of the specimen. The load cell is selected so that the tensile response from the specimen tested is between 5% and 95% of the capacity of the load cell used. Calibrate the tester according to the manufacturer's instructions.

2. Set the distance between the grips (gauge length) as per the test performed (table below).

3. Place the specimen in the flat surfaces of the grips such that the uniform width lies along a direction perpendicular to the gauge length direction. The specimen is mounted in a way that specimen stretch direction is the test direction. Secure the specimen in the upper grip, let the specimen hang slack, then close the lower grip.

4. Pre-load: Set the slack pre-load at 0.05 N/in, and pre-load crosshead speed of 13 mm/min. This means that the data collection starts when the slack is removed (at a constant crosshead speed of 13 mm/min) with a force of 0.05 N/in. Strain is calculated based on the adjusted gauge length ($l_{ini}$), which is the length of the specimen in between the grips of the tensile tester at a force of 0.05 N/in. This adjusted gauge length is taken as the initial specimen length, and it corresponds to a strain of 0%. Percent strain at any point in the test is defined as the change in length relative to the adjusted gauge length, divided by the adjusted gauge length, multiplied by 100%.

5(a). First cycle loading: Pull the specimen to the given End Point (load or strain) at a constant cross head speed as defined in the table below for the test. Report the stretched specimen length between the grips as $l_{max}$.

5(b). First cycle unloading: Hold the specimen at the End Point of step 5(a) for 30 seconds and then return the crosshead to its starting position (0% strain or initial sample length, $l_{ini}$) at a constant cross head speed defined in step 5(a) above.

5(c). Hold the specimen in the unstrained state for 1 minute.

5(d). Second cycle: Repeat Step 5(a) and 5(b):

| | Elastic and Extensible Tests | Laminate Performance Test |
|---|---|---|
| Specimen Length in the laminate stretch direction (mm) | larger than gage length | >27 |
| Specimen Width, perpendicular to laminate stretch direction (mm) | 25.4 preferred (10 mm minimum) | 25.4 |
| Gauge Length (mm) | Minimum 7 mm, maximum 25.4 mm | 25.4 |
| Test Speed (in/min) | 10 | 10 |
| End Point for Step 5(a) | 50% | 4N/in |

The force exerted on the sample during the test is recorded as a function of applied strain. From the resulting data generated, the following quantities are collected and reported.

i. Length of specimen between the grips at a slack preload of 0.05 N/in ($l_{ini}$) to the nearest 0.01 mm.

ii. Length of specimen between the grips on first cycle at the at a given strain or given force ($l_{max}$) to the nearest 0.01 mm.

iii. Length of specimen between the grips at a second cycle load force of 0.05 N/in ($l_{ext}$) to the nearest 0.001 mm.

iv. Force at 50% strain during the first load cycle to the nearest 0.01 N/in (reported as Load Force at 50%) for Laminate Performance Test set-up.

v. Force at 50% strain during the second unload cycle to the nearest 0.01 N/in (reported as Unload Force at 50%) for Laminate Performance Test set-up.

% Set is defined as $(l_{ext}-l_{ini})/(l_{max}-l_{ini})*100\%$ to the nearest 0.01%.

The testing is repeated for three separate samples and the arithmetic average is reported.

Laminate Extension Test Method

Extension of the laminate (ear, waist, cuff or other) is measured using a constant rate of extension tensile tester such as MTS Alliance. Equipment is set up and specimens are preconditioned as per the Hysteresis Test method above. The test is performed under laboratory conditions of 23° C.±2° C. and relative humidity of 50%±2%. The specimens are conditioned for 24 hours prior to testing.

Identify a corrugated portion or stretch portion on absorbent article product with bond patterns containing releasable bonds and permanent bonds. The specimen is cut from this area of the absorbent article product to dimensions listed in the table below. Specimen dimensions, gauge length, and test speed listed in the table below are used to measure Laminate Extension.

| | Laminate Extension Test |
|---|---|
| Sample Length in the laminate stretch direction (mm) | >27 |
| Sample Width, perpendicular to laminate stretch direction (mm) | 25.4 |
| Gauge Length (mm) | 25.4 |
| Test Speed (in/min) | 10 |

Test Protocol:

1) Select the appropriate grips and load cell. The grips must have one flat surface and must be wide enough to grasp the specimen along its full width. Also, the grips should provide adequate force and suitable surface area to ensure that the specimen does not slip during testing. The grips are air actuated grips designed to concentrate the entire gripping force along a single line perpendicular to the direction of testing stress having one flat surface and an opposing face from which protrudes a half round (radius=6 mm, e.g., part number: 56-163-827 from MTS Systems Corp.) or equivalent grips, to minimize slippage of the specimen. The load cell is selected so that the tensile response from the specimen tested is between 5% and 95% of the capacity of the load cell used. Calibrate the tester according to the manufacturer's instructions.

2) Set the distance between the grips (gauge length) as described in the table.

3) Place the specimen in the flat surfaces of the grips such that the uniform width lies along a direction perpendicular to the gauge length direction. Sample is mounted in a way that sample stretch direction is the test direction. Secure the specimen in the upper grip, let the specimen hang slack, then close the lower grip.

4) Pre-load: Set the slack pre-load at 0.05 N per inch, and pre-load crosshead speed of 13 mm/min. This means that the data collection starts when the slack is removed (at a constant crosshead speed of 13 mm/min) with a force of 0.05 N per inch. Strain is calculated based on the adjusted gauge length ($l_{ini}$), which is the length of the specimen in between the grips of the tensile tester at a force of 0.05 N per inch. This adjusted gauge length is taken as the initial specimen length, and it corresponds to a strain of 0%. Percent strain at any point in the test is defined as the change in length relative to the adjusted gauge length, divided by the adjusted gauge length, multiplied by 100.

5) Pull the specimen at test speed to an end point, if specified, or else pull the specimen at test speed to break. Break is defined as a sudden drop of force, by at least 50%.

Determine from the data the extension at 0.5 N/in force, the extension at 1.5 N/in force, the extension at 4 N/in force, the extension at break, and the load at break. Extension is defined as (length of the specimen between grips at given force–$l_{ini}$), and is recorded to the nearest 0.1 mm. Load at break is recorded to nearest 0.01 Newton.

Five (5) replicate specimens are run for each product example. The Average Extension at 0.5 N/in force, the Average Extension at 1.5 N/in force, the Average Extension at 4 N/in force, the Average Extension at Break, the Average Load at Break, for each of 4 specimens are reported.

Bond Ratio Test Method

A specimen is prepared as per the Laminate Extension test method. Identify an area that contains permanent and releasable bonds.

The specimen is tested as per the Laminate Extension test method above where End point for step 5 of the method is defined below in the table.

| | End Point for Step 5 |
|---|---|
| To determine bond ratio via Extension | At least 5 mm extension, eq. to ~20% strain |
| To determine bond ratio via Force | 0.5N/in force |

After the specimen is pulled to the desired extension or to the desired force, the specimen is held in that condition. The bonds in the stretched specimen are visually examined. Record the number of bonds that have released as releasable bonds and record the number of bonds that have not released as permanent bonds.

Four (4) specimens are tested. For each specimen, record number of releasable bonds and number of permanent bonds. The bond ratio for each specimen is calculated by dividing the number of permanent bonds by number of releasable bonds. The average bond ratio is determined by calculating the average (arithmetic mean) of individual bond ratios of each of the 4 specimens. The bond ratio and the average bond ratio are recorded to the nearest 0.1.

Air Permeability Test Method

The air permeability of a laminate or substrate (e.g., film, nonwoven, or article component) is determined by measuring the flow rate of standard conditioned air through a test specimen driven by a specified pressure drop. This test is particularly suited to materials having relatively high permeability to gases, such as nonwovens, apertured ear laminates and the like. ASTM D737 is used, modified as follows.

A TexTest FX 3300 instrument or equivalent is used, available from Textest AG, Switzerland, or from Advanced Testing Instruments ATI in Spartanburg SC, USA. The procedures described in the Operating Instructions for the Textest FX 3300 Air Permeability Tester manual for the Air Tightness Test and the Function and Calibration Check are followed. If a different instrument is used, similar provisions for air tightness and calibration are made according to the manufacturer's instructions.

The specimen is cut from the absorbent article part that contains releasable and permanent bonds. The specimen is tested while in a relaxed state, and area tested should contain releasable and permanent bonds.

The test is carried out using the 5 cm$^2$ area test head while pressure drop is adjusted to get a stable reading. The result is recorded to three significant digits. The average (arithmetic mean) of 5 specimens is calculated and reported as the Breathability Value (m$^3$/m$^2$/min).

In-Bag Stack Height Test Method

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e., each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 12). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Further, for all numerical ranges specified in the application it is to be appreciated that the range includes all numerical increments within the recited ranges and all ranges formed therein or thereby. For example, a numerical increment may be 0.1 mm, 1 gsm, and/or 0.1 mm².

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a topsheet;
   a backsheet;
   an absorbent core disposed between the topsheet and the backsheet; and
   at least one elastic ear comprising a laminate having an elastomeric layer and a nonwoven layer,
   wherein the laminate has a plurality of discrete primary ultrasonic bonds and a plurality of secondary ultrasonic bonds, wherein the elastomeric layer and the nonwoven layer remain permanently attached by the primary ultrasonic bonds and releasably attached by the secondary ultrasonic bonds, wherein the secondary ultrasonic bonds release when the laminate is extended greater than about 5 mm in a stretch direction, and wherein the primary ultrasonic bonds form a bond pattern upon release of the plurality of secondary ultrasonic bonds.

2. The absorbent article of claim 1, wherein a bond ratio is greater than about 1.

3. The absorbent article of claim 1, wherein the plurality of primary discrete ultrasonic bonds are greater in number than the plurality of secondary ultrasonic bonds.

4. The absorbent article of claim 1, wherein the laminate peel force is greater than or equal to 0.3 N/cm.

5. The absorbent article of claim 1, wherein the at least one elastic ear comprises a first portion and a second portion opposite the first portion, wherein the first portion of the at least one elastic ear is bonded to at least one of the topsheet and the backsheet at a chassis attachment bond.

6. The absorbent article of claim 5, wherein the plurality of secondary ultrasonic bonds do not overlap the chassis attachment bond.

7. The absorbent article of claim 1, wherein at least a portion of the plurality of secondary ultrasonic bonds are released when the absorbent article is first applied to a wearer.

8. The absorbent article of claim 1, wherein the plurality of secondary ultrasonic bonds are uniformly distributed across the laminate.

9. The absorbent article of claim 1, wherein the plurality of primary ultrasonic bonds form one or more closed cell units, and wherein at least a portion of the secondary ultrasonic bonds are disposed within the one or more closed cell units.

10. The absorbent article of claim 1, wherein the elastomeric layer is preactivated.

11. The absorbent article of claim 1, wherein the laminate comprises one or more apertures.

12. The absorbent article of claim 1, wherein the laminate comprises ink.

13. The absorbent article of claim 1, wherein the nonwoven layer of the laminate comprises at least one of a spunbonded nonwoven, carded nonwoven, hydroentangled nonwoven, air-through bonded nonwoven, and spunlaced nonwoven.

14. The absorbent article of claim 1, wherein the laminate has a plurality of corrugations.

15. The absorbent article of claim 1, wherein the laminate comprises one or more adhesive bonds.

16. The absorbent article of claim 1, wherein the laminate has an air permeability greater than about 1 m³/m²/min.

17. An absorbent article comprising:
   a topsheet;
   a backsheet;
   an absorbent core disposed between the topsheet and the backsheet; and
   at least one elastic ear comprising a laminate having an elastomeric layer and a nonwoven layer,
   wherein the laminate has a plurality of discrete primary ultrasonic bonds and a plurality of secondary ultrasonic bonds, wherein the elastomeric layer and the nonwoven layer remain permanently attached by the primary ultrasonic bonds and releasably attached by the secondary ultrasonic bonds, wherein substantially all of the secondary ultrasonic bonds release when the laminate is extended by at least 0.5 N/in force in a stretch direction, and wherein the primary ultrasonic bonds form a bond pattern upon release of the plurality of secondary ultrasonic bonds.

18. An absorbent article comprising:
   a topsheet;
   a backsheet;
   an absorbent core disposed between the topsheet and the backsheet; and
   at least one component comprising a laminate having an elastomeric layer and a nonwoven layer,
   wherein the laminate has a plurality of discrete primary ultrasonic bonds and a plurality of secondary ultrasonic bonds, wherein the elastomeric layer and the nonwoven layer remain permanently attached by the primary ultrasonic bonds and releasably attached by the secondary ultrasonic bonds, wherein substantially all of the secondary ultrasonic bonds release when the laminate is extended greater than about 5 mm in a stretch direction, and wherein the primary ultrasonic bonds form a bond pattern upon release of the plurality of secondary ultrasonic bonds.

19. The absorbent article of claim 18, wherein the component is waist gasketing feature.

20. The absorbent article of claim 18, wherein the component is an elastic ear.

\* \* \* \* \*